US010604596B2

(12) United States Patent
Cho et al.

(10) Patent No.: US 10,604,596 B2
(45) Date of Patent: Mar. 31, 2020

(54) METALLOCENE SUPPORTED CATALYST AND METHOD FOR PREPARING POLYOLEFIN USING THE SAME

(71) Applicant: LG CHEM, LTD., Seoul (KR)

(72) Inventors: Kyung Jin Cho, Daejeon (KR); Ki Soo Lee, Daejeon (KR); Sung Min Lee, Daejeon (KR); Bog Ki Hong, Daejeon (KR); Min Seok Cho, Daejeon (KR); Se Young Kim, Daejeon (KR); Chang Woan Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/558,509

(22) PCT Filed: Jun. 3, 2016

(86) PCT No.: PCT/KR2016/005925
§ 371 (c)(1),
(2) Date: Sep. 14, 2017

(87) PCT Pub. No.: WO2016/195424
PCT Pub. Date: Dec. 8, 2016

(65) Prior Publication Data

US 2018/0079841 A1   Mar. 22, 2018

(30) Foreign Application Priority Data

Jun. 5, 2015 (KR) .................. 10-2015-0080019
Jun. 2, 2016 (KR) .................. 10-2016-0069065

(51) Int. Cl.
| | | |
|---|---|---|
| *C08F 4/6592* | (2006.01) | |
| *C08F 10/02* | (2006.01) | |
| *C07F 17/00* | (2006.01) | |
| *C07F 7/08* | (2006.01) | |
| *C08F 2/34* | (2006.01) | |
| *C08F 10/00* | (2006.01) | |
| *C08F 2/04* | (2006.01) | |
| *C08F 110/02* | (2006.01) | |
| *C08F 4/659* | (2006.01) | |

(52) U.S. Cl.
CPC ............ *C08F 10/02* (2013.01); *C07F 7/0803* (2013.01); *C07F 17/00* (2013.01); *C08F 2/04* (2013.01); *C08F 2/34* (2013.01); *C08F 4/6592* (2013.01); *C08F 4/65927* (2013.01); *C08F 10/00* (2013.01); *C08F 110/02* (2013.01); *C08F 4/65912* (2013.01); *C08F 4/65916* (2013.01); *C08F 2410/02* (2013.01)

(58) Field of Classification Search
CPC .......................... C08F 4/65927; C08F 210/16
See application file for complete search history.

(56) References Cited

U.S. PATENT DOCUMENTS

| | | |
|---|---|---|
| 5,032,562 A | 7/1991 | Lo et al. |
| 5,360,921 A | 11/1994 | Kiso et al. |
| 5,525,678 A | 6/1996 | Mink et al. |
| 5,767,300 A | 6/1998 | Aulbach et al. |
| 5,780,659 A | 7/1998 | Schmid et al. |
| 5,902,867 A | 5/1999 | Muskens et al. |
| 5,914,289 A | 6/1999 | Razavi |
| 6,037,427 A | 3/2000 | Schmid et al. |
| 6,277,778 B1 | 8/2001 | Leino et al. |
| 8,299,287 B2 | 10/2012 | Dimeska et al. |
| 2008/0269439 A1 | 10/2008 | Resconi et al. |
| 2012/0259077 A1 | 10/2012 | Ha et al. |
| 2015/0266914 A1 | 9/2015 | Kashimoto et al. |

FOREIGN PATENT DOCUMENTS

| | | |
|---|---|---|
| CN | 102686616 A | 9/2012 |
| EP | 3252064 A1 | 12/2017 |
| JP | 08-165310 A | 6/1996 |
| JP | 09512848 A | 12/1997 |
| JP | 10007692 A | 1/1998 |
| JP | 2001-220404 A | 8/2001 |
| JP | 4051089 B2 | 2/2008 |
| JP | 2008050278 A | 3/2008 |
| JP | 2008540714 A | 11/2008 |
| JP | 4590037 B2 | 12/2010 |
| JP | 2013100481 A | 5/2013 |
| JP | 5466826 B2 | 4/2014 |
| JP | 2014111568 A | 6/2014 |
| JP | 2014-156480 A | 8/2014 |
| JP | 2015063515 A | 4/2015 |
| KR | 1020040076965 A | 9/2004 |
| KR | 1020150058054 A | 5/2015 |
| KR | 1020150058938 A | 5/2015 |

(Continued)

OTHER PUBLICATIONS

Grimmer, et al.: "Zirconium bis-indenyl compounds. The influence of substituents on the ethene polymerization behavior of 1- and 2-substituted (R-Ind)2ZrCl2/MAO catalysts", XP004329870, Journal of Organometalic Chemistry, Elsevier, vol. 642, No. 1-2, Jan. 18, 2002, pp. 195-202.

Andreas C. Möller, Synthesis, structure, and ethene polymerisation catalysis of 1- or 2-silyl substituted bis [indenyl]zirconium(IV) dichlorides, Macromolecules 2001, 34, 2072-2082.

(Continued)

*Primary Examiner* — Caixia Lu

(74) *Attorney, Agent, or Firm* — Dentons US LLP

(57) ABSTRACT

The present disclosure relates to a novel metallocene supported catalyst, and a method for preparing a polyolefin using the same. The metallocene supported catalyst according to the present disclosure exhibits a high polymerization activity even when the metallocene compound is supported on a support, thereby showing an excellent activity and preparing a polyolefin having a high molecular weight.

13 Claims, No Drawings

(56) References Cited

FOREIGN PATENT DOCUMENTS

| KR | 1020170076642 A | 7/2017 |
| WO | 03/050131 A1 | 6/2003 |
| WO | 2009054832 A1 | 4/2009 |

OTHER PUBLICATIONS

Reko Leino, Syndiospecific Propylene Polymerization . . . , Dalton Trans., 2004, pp. 1578-1589.

METALLOCENE SUPPORTED CATALYST AND METHOD FOR PREPARING POLYOLEFIN USING THE SAME

CROSS REFERENCE TO RELATED APPLICATIONS

This application is a National Stage Application of International Application No. PCT/KR2016/005925, filed Jun. 3, 2016, and claims the benefit of Korean Patent Application No. 10-2016-0069065, filed on Jun. 2, 2016, Korean Patent Application No. 10-2015-0080019, filed on Jun. 5, 2015, contents of which are incorporated herein by reference in their entirety for all purposes as if fully set forth below.

The present disclosure relates to a novel metallocene supported catalyst, and a method for preparing a polyolefin using the same.

BACKGROUND OF ART

Olefin polymerization catalyst systems may be divided into Ziegler-Natta and metallocene catalysts, and these highly active catalyst systems have been developed in accordance with their characteristics. Ziegler-Natta catalyst has been widely applied to commercial processes since it was developed in the 1950's. However, since the Ziegler-Natta catalyst is a multi-site catalyst in which a plurality of active sites are mixed, it has a feature that a resulting polymer has a broad molecular weight distribution. Also, since a compositional distribution of comonomers is not uniform, there is a problem that it is difficult to obtain desired physical properties.

Meanwhile, the metallocene catalyst includes a main catalyst having a transition metal compound as a main component and an organometallic compound cocatalyst having aluminum as a main component. Such a catalyst is a single-site catalyst which is a homogeneous complex catalyst, and offers a polymer having a narrow molecular weight distribution and a uniform compositional distribution of comonomers, due to the single site characteristics. The stereoregularity, copolymerization characteristics, molecular weight, crystallinity, etc. of the resulting polymer may be controlled by changing a ligand structure of the catalyst and polymerization conditions.

U.S. Pat. No. 5,032,562 discloses a method for preparing a polymerization catalyst by supporting two different transition metal catalysts on one support. This catalyst is prepared by supporting a titanium (Ti)-based Ziegler-Natta catalyst which produces a high molecular weight polymer and a zirconium (Zr)-based metallocene catalyst which produces a low molecular weight polymer on one support, and results in a bimodal molecular weight distribution. This catalyst has disadvantage in that the supporting procedure is complicated and morphology of polymers is poor due to a cocatalyst.

U.S. Pat. No. 5,525,678 discloses a method for using a catalyst system for olefin polymerization, in which a metallocene compound and a non-metallocene compound are simultaneously supported on a support to conduct simultaneous polymerization of a high molecular weight polymer and a low molecular weight polymer. However, there are disadvantages that the metallocene compound and non-metallocene compound must be separately supported and the support must be pretreated with various compounds for supporting.

U.S. Pat. No. 5,914,289 discloses a method for controlling a molecular weight and a molecular weight distribution of polymers using metallocene catalysts which are respectively supported on supports. However, a large amount of solvent and a long period of time are required to prepare the supported catalysts, and a process of supporting metallocene catalysts on the respective supports is troublesome.

Korean Patent Application No. 2003-12308 discloses a method for controlling molecular weight distributions of polymers, in which the polymerization is performed while changing a combination of catalysts in a reactor by supporting a dinuclear metallocene catalyst and a mononuclear metallocene catalyst on a support together with an activating agent. However, this method has limitations in simultaneously realizing the characteristics of respective catalysts. In addition, there is a disadvantage that the metallocene catalysts are departed from a supported component of the resulting catalyst to cause fouling in the reactor.

Therefore, to solve the above drawbacks, there is a continuous demand for a method for preparing polyolefins with desired physical properties by easily preparing a hybrid supported metallocene catalyst having an excellent activity.

DETAILED DESCRIPTION OF THE INVENTION

Technical Problem

The present disclosure provides a metallocene supported catalyst having excellent activity and capable of producing an olefin-based polymer having a high molecular weight, a method for preparing a polyolefin using the same, and a polyolefin prepared by using the same.

Particularly, the present disclosure provides a metallocene compound which exhibits a high polymerization activity even when it is supported on a support, and may be used to prepare a polyolefin having a high molecular weight, a supported catalyst including the same, a method for preparing a polyolefin using the same, and a polyolefin prepared by using the same.

Technical Solution

The present disclosure provides a metallocene supported catalyst comprising a metallocene compound represented by the following Chemical Formula 1; a cocatalyst compound; and a support.

[Chemical Formula 1]

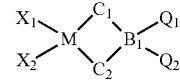

wherein in Chemical Formula 1,

M is a Group 4 transition metal;

$B_1$ is carbon, silicon, or germanium;

$Q_1$ and $Q_2$ are the same as or different from each other, and are each independently hydrogen, halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

$X_1$ and $X_2$ are the same as or different from each other, and are each independently halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group;

$C_1$ is represented by the following Chemical Formula 2a, and $C_2$ is represented by the following Chemical Formula 2b, Chemical Formula 2c, Chemical Formula 2d, or Chemical Formula 2e;

[Chemical Formula 2a]

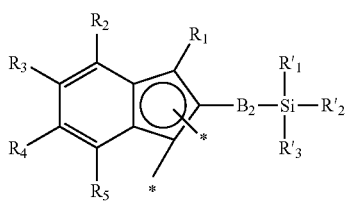

[Chemical Formula 2b]

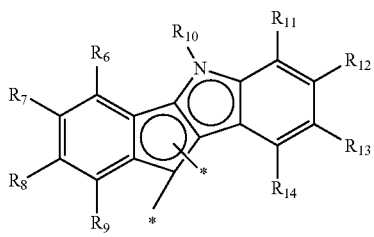

[Chemical Formula 2c]

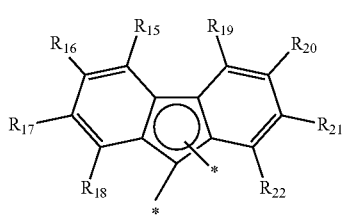

[Chemical Formula 2d]

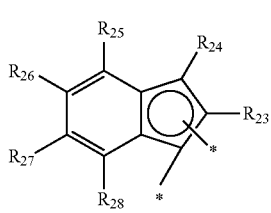

[Chemical Formula 2e]

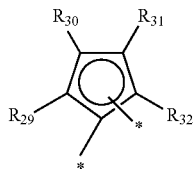

wherein, in Chemical Formulae 2a, 2b, 2c, 2d, and 2e, $B_2$ is a single bond or a C1 to C3 alkylene group,

* is a site to which M or $B_1$ of Chemical Formula 1 is connected, $R_1$ to $R_5$ are the same as or different from each other, and are each independently hydrogen, halogen, a C1 to C20 alkyl group, a C2 to C20 alkenyl group, an C1 to C20 ether group, a C1 to C20 alkoxy group, a C6 to C20 aryl group, a C7 to C20 alkylaryl group, or a C7 to C20 arylalkyl group, $R_6$ to $R_{32}$ are the same as or different from each other, and are each independently hydrogen, halogen, a C1 to C20 alkyl group, a C1 to C20 alkoxy group, a C6 to C20 aryl group, a C7 to C20 alkylaryl group, or a C7 to C20 arylalkyl group, $R'_1$ to $R'_3$ are the same as or different from each other, and are each independently hydrogen, halogen, or a C1 to C20 alkyl group.

Also, the present disclosure provides a method for preparing a polyolefin, the method comprising polymerizing olefin-based monomers in the presence of the metallocene supported catalyst.

Also, the present disclosure provides a polyolefin prepared by the preparation method.

Advantageous Effects

A metallocene supported catalyst according to the present disclosure may be used for the preparing a polyolefin, may have excellent activity, and may be used to prepare a polyolefin having a relatively high molecular weight.

Particularly, the metallocene catalyst compound of the present disclosure may exhibit a high polymerization activity even when it is supported on a support, thereby preparing a polyolefin having a high molecular weight.

Furthermore, the activity of the catalyst may be maintained for a long residence time in a reactor because of its long life time.

DETAILED DESCRIPTION OF THE EMBODIMENTS

In the present disclosure, the terms "the first", "the second", and the like are used to describe a variety of components, and these terms are merely employed to differentiate a certain component from other components.

Further, the terms used in this description are just for explaining exemplary embodiments and it is not intended to restrict the present disclosure. The singular expression may include the plural expression unless it is differently expressed contextually. It must be understood that the term "include", "equip", or "have" in the present description is only used for designating the existence of characteristics taken effect, numbers, steps, components, or combinations thereof, and do not exclude the existence or the possibility of addition of one or more different characteristics, numbers, steps, components of combinations thereof beforehand.

The present disclosure may be variously modified and have various forms, and specific examples of the present disclosure are explained in this description. However, it is not intended to limit the present disclosure to the specific examples and it must be understood that the present disclosure includes every modifications, equivalents, or replacements included in the spirit and technical scope of the present disclosure.

Hereinafter, the present disclosure will be described in more detail.

A metallocene supported catalyst according to the present disclosure is characterized in that it includes a metallocene compound represented by the following Chemical Formula 1; a cocatalyst compound; and a support.

[Chemical Formula 1]

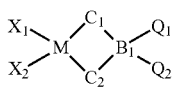

wherein in Chemical Formula 1,

M is a Group 4 transition metal;

$B_1$ is carbon, silicon, or germanium;

$Q_1$ and $Q_2$ are the same as or different from each other, and are each independently hydrogen, halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

$X_1$ and $X_2$ are the same as or different from each other, and are each independently halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group;

$C_1$ is represented by the following Chemical Formula 2a, and $C_2$ is represented by the following Chemical Formula 2b, Chemical Formula 2c, Chemical Formula 2d, or Chemical Formula 2e;

[Chemical Formula 2a]

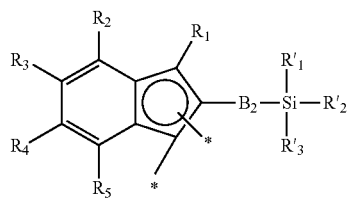

[Chemical Formula 2b]

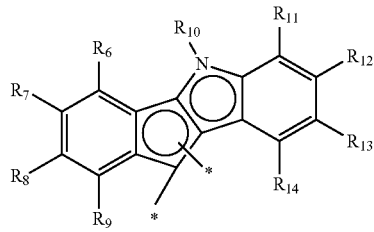

[Chemical Formula 2c]

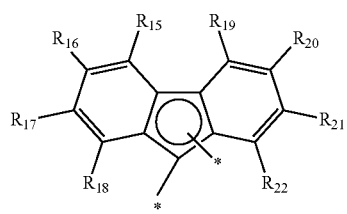

[Chemical Formula 2d]

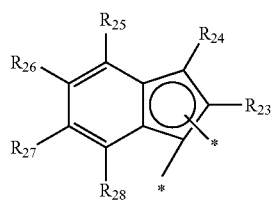

[Chemical Formula 2e]

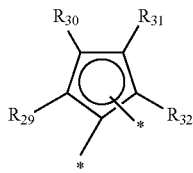

wherein, in Chemical Formulae 2a, 2b, 2c, 2d, and 2e, $B_2$ is a single bond or a C1 to C3 alkylene group, \* is a site to which M or $B_1$ of Chemical Formula 1 is connected, $R_1$ to $R_5$ are the same as or different from each other, and are each independently hydrogen, halogen, a C1 to C20 alkyl group, a C2 to C20 alkenyl group, an C1 to C20 ether group, a C1 to C20 alkoxy group, a C6 to C20 aryl group, a C7 to C20 alkylaryl group, or a C7 to C20 arylalkyl group, $R_6$ to $R_{32}$ are the same as or different from each other, and are each independently hydrogen, halogen, a C1 to C20 alkyl group, a C1 to C20 alkoxy group, a C6 to C20 aryl group, a C7 to C20 alkylaryl group, or a C7 to C20 arylalkyl group, $R'_1$ to $R'_3$ are the same as or different from each other, and are each independently hydrogen, halogen, or a C1 to C20 alkyl group.

The metallocene compound may maintain an excellent activity and a polymerization property while producing a polyolefin having a high molecular weight by combination of substituents represented by Chemical Formulae 2a and 2b to 2e by applying Chemical Formula 2a having a particular substituent to one of $C_1$ and $C_2$ and applying Chemical Formula 2b to 2e to the other of $C_1$ and $C_2$ in Chemical Formula 1.

In the metallocene supported catalyst according to the present disclosure, the substituents of Chemical Formula 1 are more specifically explained as follows.

The C1 to C20 alkyl group may include a linear or branched alkyl group, and specifically, it may be a methyl group, an ethyl group, a propyl group, an isopropyl group, an n-butyl group, a tert-butyl group, a pentyl group, a hexyl group, a heptyl group, an octyl group, or the like, but is not limited thereto.

The C2 to C20 alkenyl group may include a linear or branched alkenyl group, and specifically, it may be an allyl group, an ethenyl group, a propenyl group, a butenyl group, a pentenyl group, or the like, but is not limited thereto.

The C6 to C20 aryl group may include a single ring aryl group or a condensed ring aryl group, and specifically, it may be a phenyl group, a biphenyl group, a naphthyl group, a phenanthrenyl group, a fluorenyl group, or the like, but is not limited thereto.

The C5 to C20 heteroaryl group may include a single ring heteroaryl group or a condensed ring heteroaryl group, and specifically, it may be a carbazolyl group, a pyridyl group, a quinoline group, an isoquinoline group, a thiophenyl group, a furanyl group, an imidazole group, an oxazolyl group, a thiazolyl group, a triazine group, a tetrahydropyranyl group, a tetrahydrofuranyl group, or the like, but is not limited thereto.

The C1 to C20 alkoxy group may be a methoxy group, an ethoxy group, a phenyloxy group, a cyclohexyloxy group, a tert-butoxyhexyl group, or the like, but is not limited thereto.

The Group 4 transition metal may be titanium, zirconium, hafnium, or the like, but is not limited thereto.

In the metallocene compound according to the present disclosure, it is more preferable that $R_1$ to $R_5$ in Chemical Formulae 2a, 2b, 2c, 2d, and 2e are each independently hydrogen, halogen, a methyl group, an ethyl group, a propyl group, an isopropyl group, an n-butyl group, a tert-butyl group, a pentyl group, a hexyl group, a heptyl group, an octyl group, an ethylene group, a propylene group, a butylene group, a phenyl group, a benzyl group, a naphthyl group, a halogen group, an ether group, a dimethyl ether group, a methoxy group, an ethoxy group, or a tert-butoxyhexyl group, and $R_6$ to $R_{32}$ in in Chemical Formulae 2a, 2b, 2c, 2d, and 2e are each independently hydrogen, halogen, a methyl group, an ethyl group, a propyl group, an isopropyl group, an n-butyl group, a tert-butyl group, a pentyl group, a hexyl group, a heptyl group, an octyl group, an ethylene group, a propylene group, a butylene group, a phenyl group, a benzyl group, a naphthyl group, a halogen group, an ether group, a dimethyl ether group, a methoxy group, an ethoxy group, or a tert-butoxyhexyl group, but is not limited thereto.

In the metallocene compound according to the present disclosure, it is preferable that $Q_1$ and $Q_2$ in Chemical Formula 1 are each independently hydrogen, a methyl group, an ethyl group, a propyl group, an isopropyl group, an n-butyl group, a tert-butyl group, a methoxymethyl group, a tert-butoxymethyl group, a 1-ethoxyethyl group, a 1-methyl-1-methoxyethyl group, a tert-butoxyhexyl group, a tetrahydropyranyl group, or a tetrahydrofuranyl group, but is not limited thereto.

In the metallocene compound according to the present disclosure, $B_1$ in Chemical Formula 1 is preferably silicon (Si), but is not limited thereto.

Specifically, the metallocene compound of the Chemical Formula 1 is characterized in that the substituent of the Chemical Formula 2a includes a silylalkyl group such as trimethylsilyl methyl.

More specifically, as the indene derivative of the Chemical Formula 2a has a silylalkyl group at the 2-position carbon of the indene, the vicinity of the active site is opened only in one direction due to the steric effect by the substituent, and thus, the polymer can be grown only in one direction. In addition, chain elongation can occur relatively strongly, because it is difficult to access to monomers or reagents that cause chain transfer and to eliminate hydrogen at the beta site in the molecule (beta-elimination). Therefore, the olefin polymer having a relatively high molecular weight can be polymerized with high activity as compared with the case of using another metallocene compound having a similar structure.

In particular, since the compound has the indenyl group represented by the above Chemical Formula 2a containing a silylalkyl group at 2-position carbon only on one side, it has smaller steric hindrance effect than the compound having a silylalkyl group on both sides. Therefore, when the ethylene-alpha olefin copolymerization proceeds, the content of the comonomer can be effectively increased even when a relatively large alpha-olefin such as 1-hexene, 1-heptene or 1-octene is used.

In addition, the compound forms a structure in which the indeno indole derivative represented by the following Chemical Formula 2b, the fluorenyl derivative represented by the following Chemical Formula 2c, the indene derivative represented by the following Chemical Formula 2d, and the cyclopentadiene derivative represented by the following Chemical Formula 2e are cross-linked by a bridge, and exhibits a high polymerization activity by having a non-covalent electron pair capable of acting as a Lewis base in a ligand structure.

According to an embodiment of the present disclosure, a specific example of the compound represented by Chemical Formula 2a may be a compound represented by any one of the following structural formulae, but is not limited thereto.

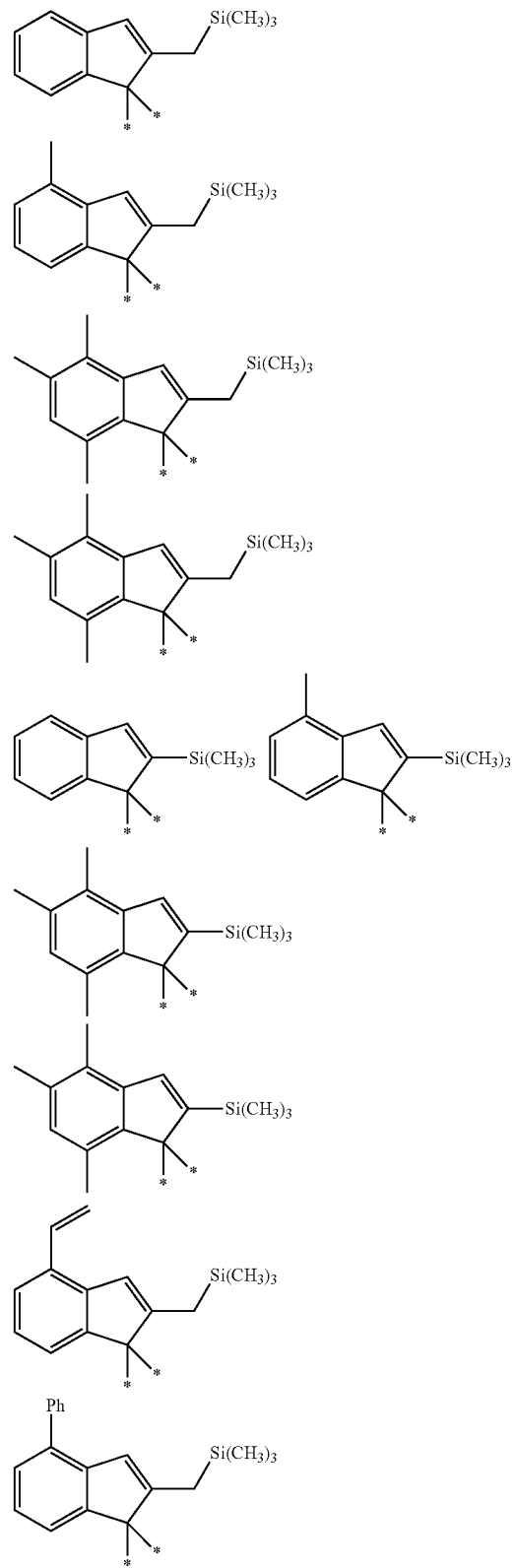

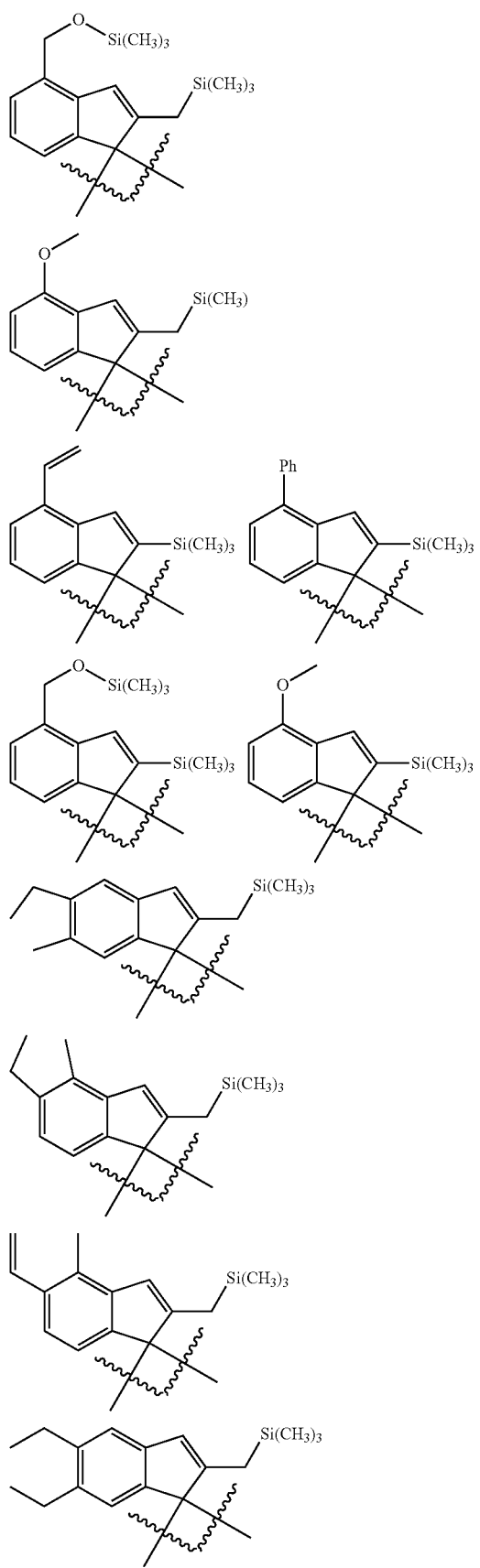
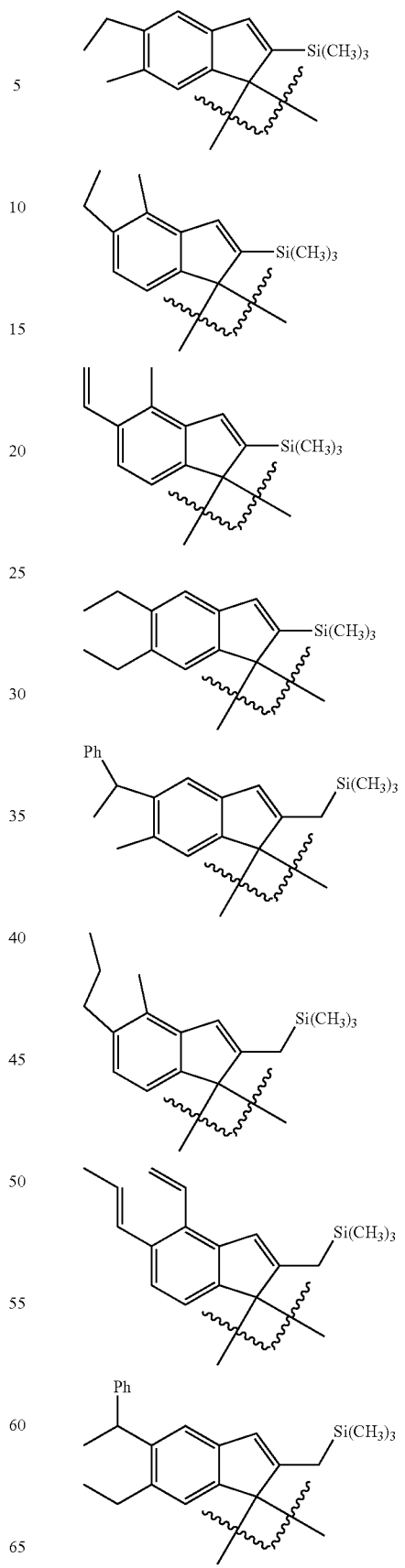

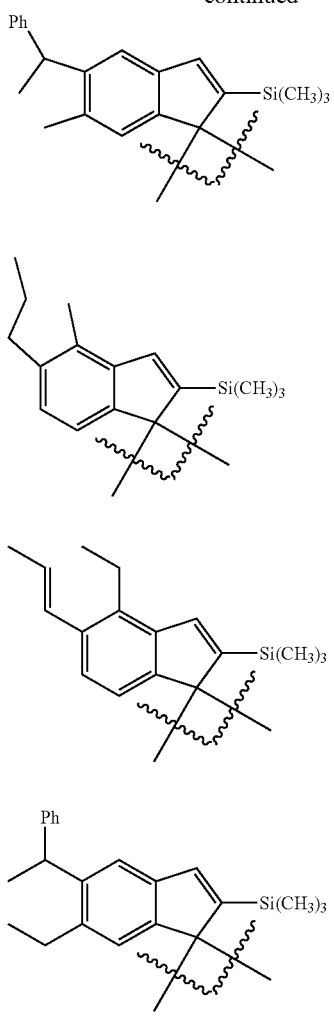
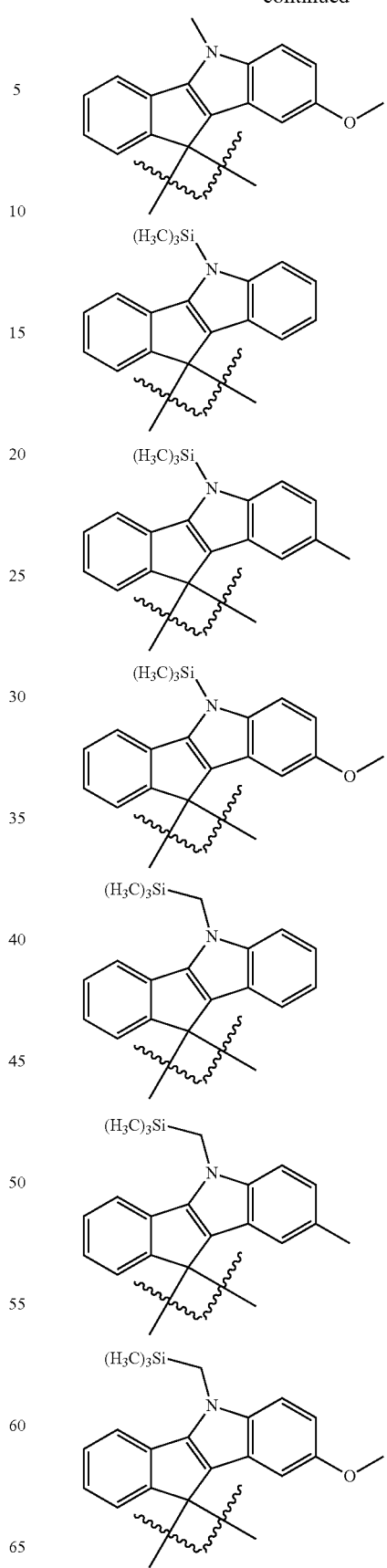
According to an embodiment of the present disclosure, a specific example of the compound represented by Chemical Formula 2b may be a compound represented by any one of the following structural formulae, but is not limited thereto.
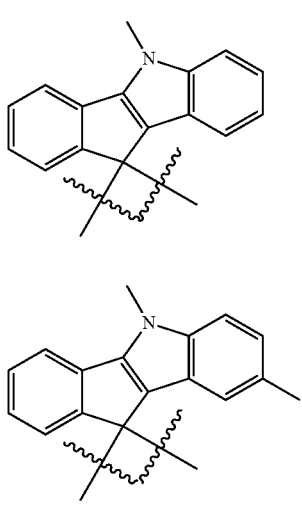

-continued
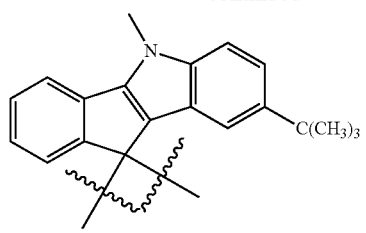
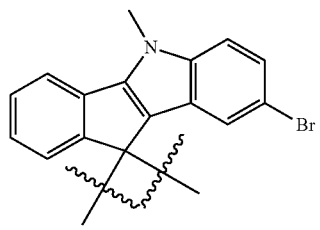
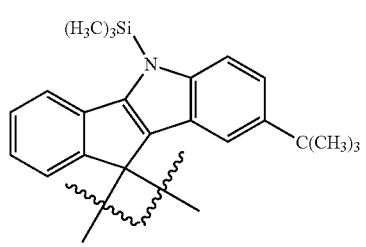
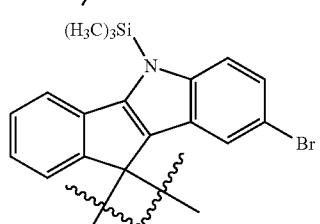
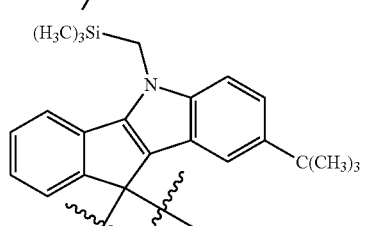
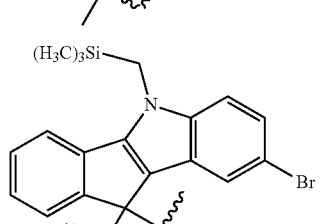
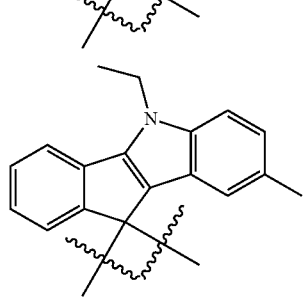
-continued
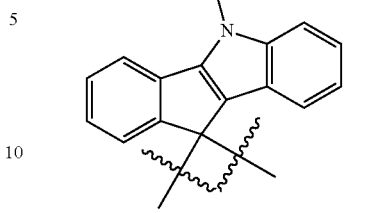
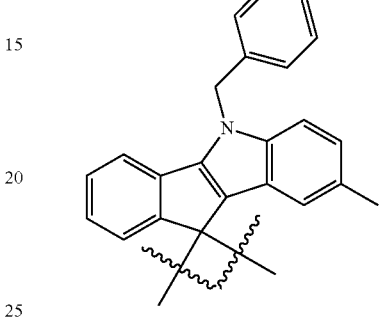
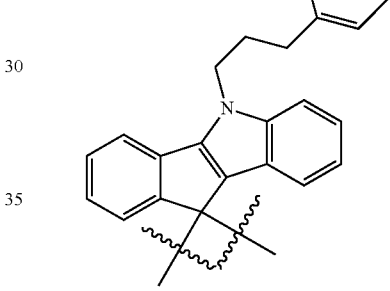
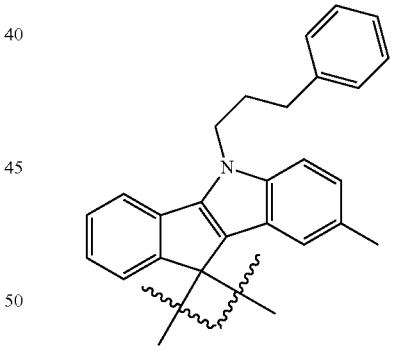
According to an embodiment of the present disclosure, a specific example of the compound represented by Chemical Formula 2c may be a compound represented by any one of the following structural formulae, but is not limited thereto.
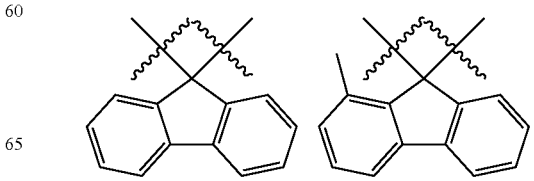

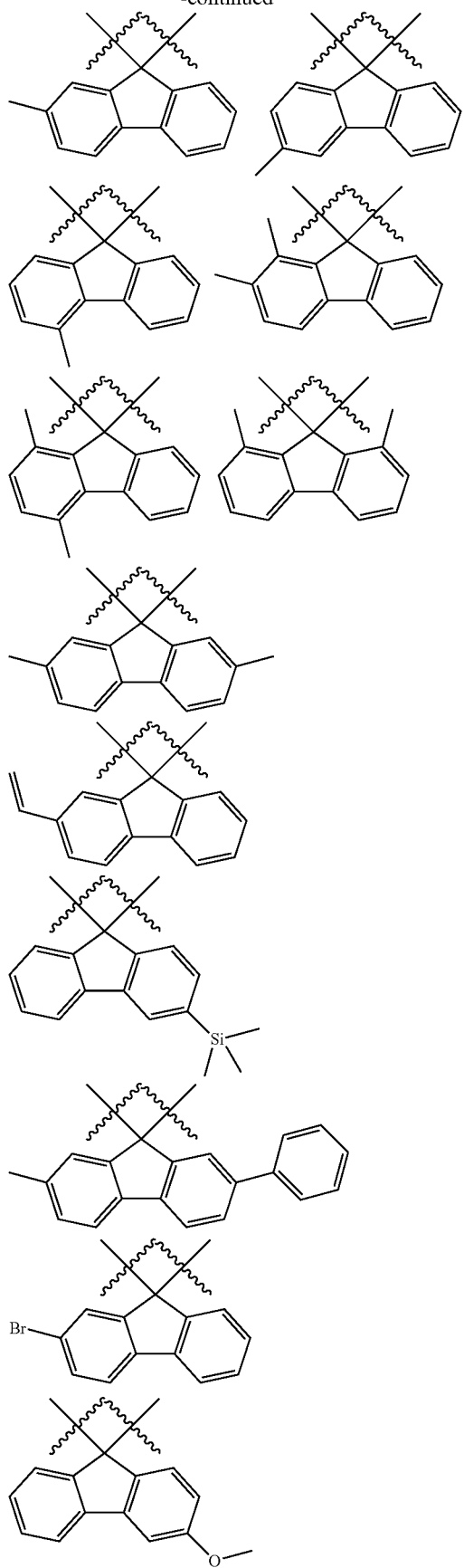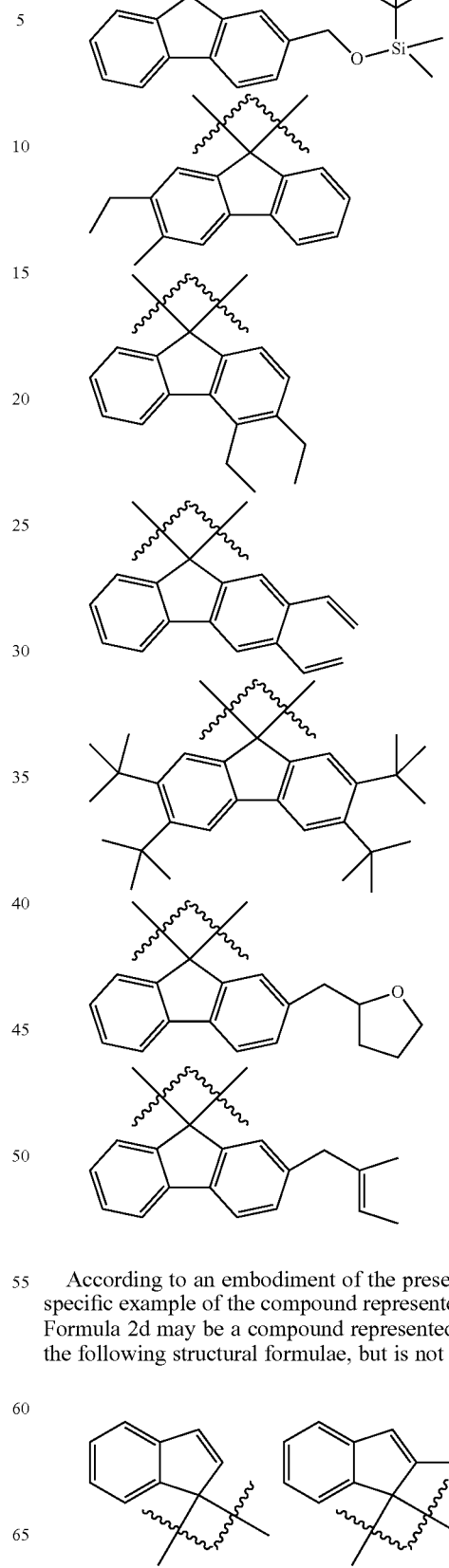
According to an embodiment of the present disclosure, a specific example of the compound represented by Chemical Formula 2d may be a compound represented by any one of the following structural formulae, but is not limited thereto.

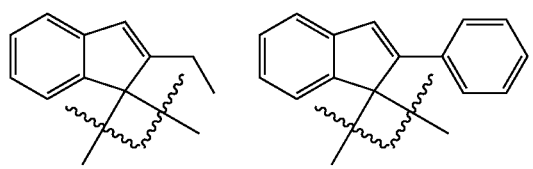

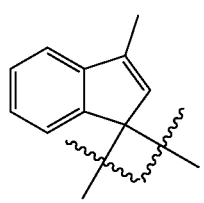

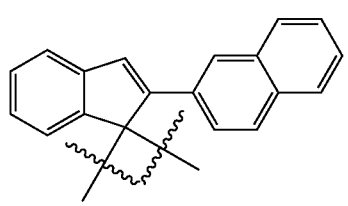

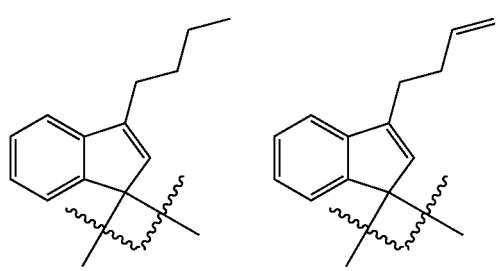

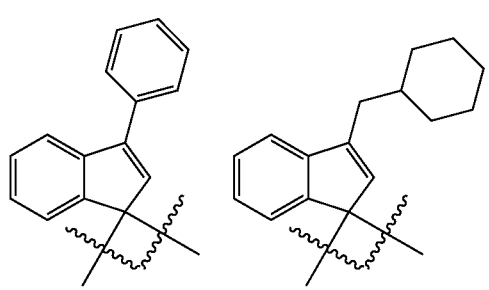

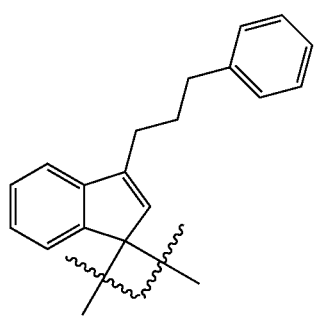

According to an embodiment of the present disclosure, a specific example of the compound represented by Chemical Formula 2d may be a compound represented by any one of the following structural formulae, but is not limited thereto.

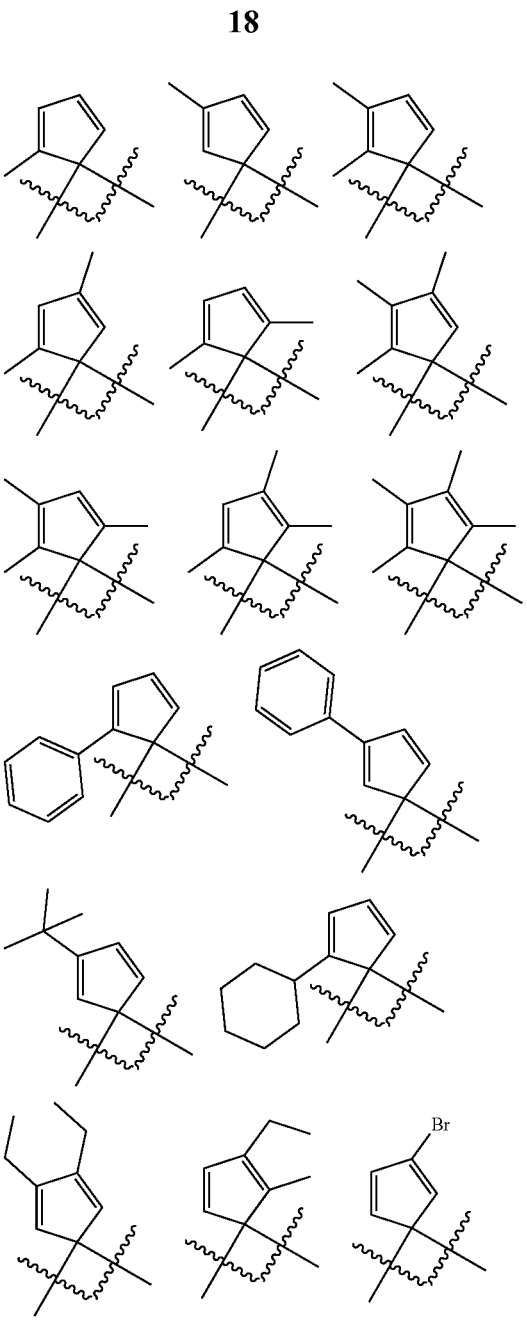

According to an embodiment of the present disclosure, a specific example of the compound represented by Chemical Formula 1 may be a compound represented by any one of the following structural formulae, but is not limited thereto.

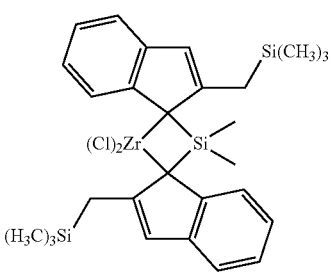

-continued

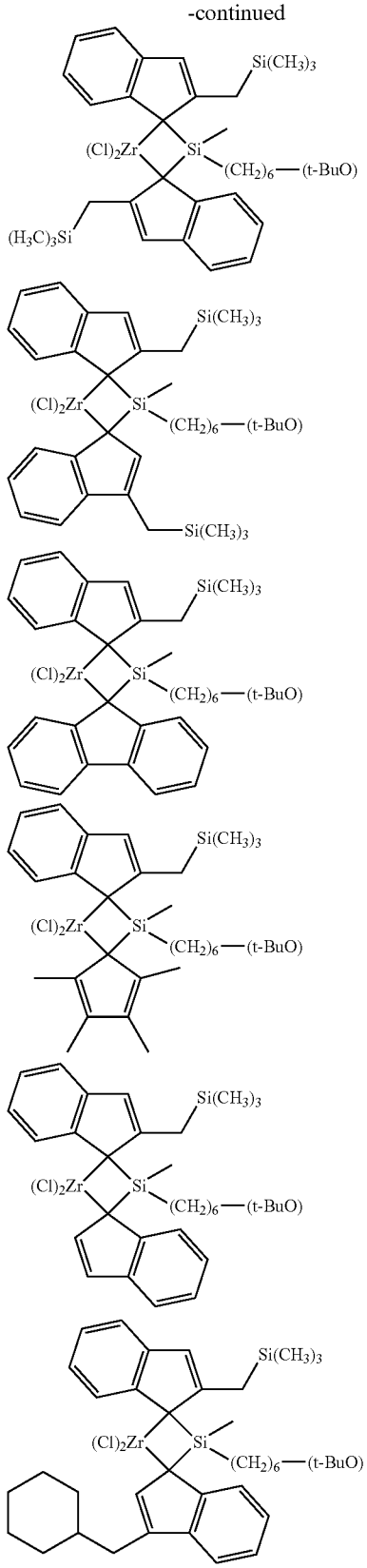

The metallocene compound above may have excellent activity and may polymerize an olefin-based polymer having a high molecular weight.

Further, the metallocene compound according to the present disclosure may polymerize an olefin-based polymer having a middle or high molecular weight with still high activity even when a polymerization reaction is carried out using a supported catalyst which is prepared by supporting the metallocene compound on a support. Therefore, the metallocene compound may prepare an olefin-based polymer satisfying the high molecular weight characteristic without a decrease in activity even when it is heterogeneously used with a catalyst having different characteristic, and thus the olefin-based polymer having a middle or high molecular weight and a wide molecular weight distribution may be easily prepared.

According to an embodiment of the present disclosure, the metallocene compound of Chemical Formula 1 may be obtained by connecting the indene derivative and the cyclopentadiene derivative with a bridge compound to prepare a ligand compound, and carrying out a metallation by adding a metal precursor compound, but is not limited to thereto.

More specifically, for example, after preparing a lithium salt by reacting the indene derivative with an organic lithium compound such as n-BuLi, a halogenated compound of a bridge compound is mixed therewith and then this mixture is reacted to prepare the ligand compound. After mixing the ligand compound or the lithium salt thereof and the metal precursor compound, and reacting them for about 12 to 24 hours until the reaction is completed, the reaction mixture may be filtered and dried under reduced pressure to obtain the metallocene compound represented by Chemical Formula 1.

A preparation method of the metallocene compound is concretely explained in the following examples.

The metallocene supported catalyst of the present disclosure may further include one or more of cocatalyst compounds represented by the following Chemical Formula 3, Chemical Formula 4, and Chemical Formula 5, in addition to the metallocene compound.

$$—[Al(R_a)—O]_n—$$ [Chemical Formula 3]

in Chemical Formula 3,
$R_a$ may be the same as or different from each other, and each independently halogen; C1 to C20 hydrocarbon; or halogen-substituted C1 to C20 hydrocarbon; and
n is an integer of 2 or more;

$$J(R_b)_3$$ [Chemical Formula 4]

in Chemical Formula 4,
$R_b$ are the same as defined in Chemical Formula 3; and
J is aluminum or boron;

$$[E-H]+[ZA_4]- \text{ or } [E]+[ZA_4]-$$ [Chemical Formula 5]

in Chemical Formula 5,
E is a neutral or cationic Lewis acid;
H is a hydrogen atom;
Z is a Group 13 element; and
A may be the same as or different from each other, and each independently a C6 to C20 aryl group or a C1 to C20 alkyl group, of which one or more hydrogen atoms are substituted or unsubstituted with halogen, C1 to C20 hydrocarbon, alkoxy, or phenoxy.

Examples of the compound represented by Chemical Formula 3 may include methylaluminoxane, ethylaluminoxane, isobutylaluminoxane, butylaluminoxane or the like, and a more preferred compound may be methylaluminoxane.

Examples of the compound represented by Chemical Formula 4 may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, tri isopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron or the like, and a more preferred compound may be selected from trimethylaluminum, triethylaluminum, and triisobutylaluminum.

Examples of the compound represented by Chemical Formula 5 may include triethylammonium tetraphenylboron, tributylammonium tetraphenylboron, trimethylammonium tetraphenylboron, tripropylammonium tetraphenylboron, trimethylammonium tetra(p-tolyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetrapentafluorophenylaluminum, diethylammonium tetrapentatetraphenylaluminum, triphenylphosphonium tetraphenylaluminum, trimethylphosphonium tetraphenylaluminum, tripropylammonium tetra(p-tolyl)boron, triethylammonium tetra(o,p-dimethylphenyl)boron, tributylammonium tetra(p-trifluoromethylphenyl)boron, triphenylcarboniumtetra(p-trifluoromethylphenyl)boron, triphenylcarboniumtetrapentafluorophenylboron, etc.

Alumoxane may be preferably used, and methylalumoxane (MAO) which is an alkyl alumoxane may be more preferably used.

The metallocene supported catalyst of the present disclosure may be prepared by a first method including the steps of 1) contacting the metallocene compound represented by Chemical Formula 1 with the compound represented by Chemical Formula 3 or Chemical Formula 4 to obtain a mixture; and 2) adding the compound represented by Chemical Formula 5 to the mixture.

Further, the metallocene supported catalyst of the present disclosure may be prepared by a second method of contacting the metallocene compound represented by Chemical Formula 1 with the compound represented by Chemical Formula 3.

In the first method of preparing the supported catalyst, a molar ratio of the metallocene compound represented by Chemical Formula 1/the compound represented by Chemical Formula 3 or Chemical Formula 4 is preferably 1/5,000 to 1/2, more preferably 1/1,000 to 1/10, and most preferably 1/500 to 1/20.

When the molar ratio of the metallocene compound represented by Chemical Formula 1/the compound represented by Chemical Formula 3 or Chemical Formula 4 exceeds 1/2, there is a problem that the metal compound is not completely alkylated due to the small amount of the alkylating agent, and when the molar ratio is less than 1/5,000, the alkylation of the metal compound is accomplished, but there is a problem that the alkylated metal compound is not completely activated due to a side reaction between the remaining excess alkylating agent and an activator of Chemical Formula 6.

Furthermore, a molar ratio of the metallocene compound represented by Chemical Formula 1/the compound represented by Chemical Formula 5 is preferably 1/25 to 1, more preferably 1/10 to 1, and most preferably 1/5 to 1. When the molar ratio of the metallocene compound represented by Chemical Formula 1/the compound represented by Chemical Formula 5 exceeds 1, the activity of the prepared supported catalyst is deteriorated because the activator is relatively small in quantity and the metal compound is not completely activated. When the molar ratio is less than 1/25, the activation of the metal compound is completely accomplished, but cost of the supported catalyst is not economical or purity of the polymer to be prepared is decreased due to the remaining excess activator.

In the second method of preparing the supported catalyst, a molar ratio of the metallocene compound represented by Chemical Formula 1/the compound represented by Chemical Formula 3 is preferably 1/10,000 to 1/10, more preferably 1/5,000 to 1/100, and most preferably 1/3,000 to 1/500. When the molar ratio exceeds 1/10, the activity of the prepared supported catalyst is deteriorated because the activator is relatively small in quantity and the metal compound is not completely activated. When the molar ratio is less than 1/10,000, the activation of the metal compound is completely accomplished, but cost of the supported catalyst is not economical or purity of the polymer to be prepared is decreased due to the remaining excess activator.

As a reaction solvent used upon preparation of the supported catalyst, a hydrocarbon solvent such as pentane, hexane, heptane, etc., or an aromatic solvent such as benzene, toluene, etc., may be used.

Furthermore, the supported catalyst may include the metallocene compound and the cocatalyst compound in the form of being supported on a support.

When the metallocene compound and the cocatalyst compound are used in the form of being supported on a support, the metallocene compound may be included in an amount of about 0.5 parts by weight to about 20 parts by weight and the cocatalyst may be included in an amount of about 1 part by weight to about 1,000 parts by weight, based on 100 parts by weight of the support. Preferably, the metallocene compound may be included in an amount of about 1 part by weight to about 15 parts by weight and the cocatalyst may be included in an amount of about 10 parts by weight to about 500 parts by weight, based on 100 parts by weight of the support. Most preferably, the metallocene compound may be included in an amount of about 1 part by weight to about 100 parts by weight and the cocatalyst may be included in an amount of about 40 parts by weight to about 150 parts by weight, based on 100 parts by weight of the support.

In the metallocene supported catalyst of the present disclosure, a weight ratio of the total transition metals included in the metallocene compound to the support may be 1:10 to 1:1,000. When the support and the metallocene compound are included at the above weight ratio, an optimal shape may be obtained. Further, a weight ratio of the cocatalyst compound to the support may be 1:1 to 1:100. When the cocatalyst and the metallocene compound are included at the above weight ratio, activity and a microstructure of the polymer may be optimized.

Meanwhile, as long as the support is a metal, a metal salt, or a metal oxide which is commonly used in supported catalysts, there is no limitation in the constitution. Specifically, it may include any support selected from the group consisting of silica, silica-alumina, and silica-magnesia. The support may be dried at a high temperature. Generally, the support may include an oxide, a carbonate, a sulfate, or a nitrate of a metal, such as $Na_2O$, $K_2CO_3$, $BaSO_4$ and $Mg(NO_3)_2$, etc.

An amount of hydroxy groups (—OH) on the surface of the support is preferably as small as possible, but it is practically difficult to eliminate all hydroxy groups. The amount of hydroxy groups may be controlled by the preparation method, the preparation conditions, the drying conditions (temperature, time, drying method, etc.), etc. of the support, and the amount is preferably 0.1 mmol/g to 10 mmol/g, more preferably 0.1 mmol/g to 1 mmol/g, and much more preferably 0.1 mmol/g to 0.5 mmol/g. In order to reduce the side-reaction by a few hydroxy groups remaining after drying, a support from which hydroxy groups are chemically eliminated while preserving highly reactive siloxane groups that participate in supporting may be used.

The metallocene supported catalyst according to the present disclosure may be used as it is in polymerization of olefin-based monomers. Also, the metallocene supported catalyst according to the present disclosure may be prepared as a pre-polymerized catalyst by contacting the catalyst with an olefin-based monomer. For example, it may be prepared as a pre-polymerized catalyst by contacting the catalyst with an olefin-based monomer such as ethylene, propylene, 1-butene, 1-hexene, 1-octene, etc.

The metallocene supported catalyst according to the present disclosure is prepared, for example, by supporting the cocatalyst compound on the support, and supporting the metallocene compound represented by Chemical Formula 1 on the support. Between the respective supporting steps, washing may be further carried out by using a solvent.

The process of preparing the metallocene supported catalyst as above may be carried out at a temperature of about 0 to about 100° C. under a normal pressure, but is not limited thereto.

Meanwhile, the present disclosure provides a method for preparing a polyolefin by polymerizing olefin-based monomers in the presence of the metallocene supported catalyst, and a polyolefin prepared by the above preparation method.

The olefin-based monomer may include ethylene, alpha-olefin, cyclic olefin, diene olefin or triene olefin having two or more double bonds.

Specific examples of the olefin-based monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norbornadiene, ethyl idenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, 3-chloromethylstyrene, etc., and these monomers may be copolymerized by mixing two or more thereof.

The polymerization reaction may be carried out by homopolymerizing one type of olefin-based monomer or copolymerizing two or more types of monomers, using a continuous slurry polymerization reactor, a loop slurry reactor, a gas phase reactor, or a solution reactor.

The metallocene supported catalyst may be used after being dissolved or diluted in an aliphatic hydrocarbon solvent having 5 to 12 carbon atoms, for example, pentane, hexane, heptane, nonane, decane, and isomers thereof, an aromatic hydrocarbon solvent such as toluene and benzene, or a hydrocarbon solvent substituted with a chlorine atom such as dichloromethane and chlorobenzene. It is preferable that the solvent is used, after a small amount of water, air or the like acting as a catalyst poison is removed by treating with a small amount of alkyl aluminum, or using an additional cocatalyst.

The polymerization of the olefin-based monomer may be carried out at a temperature of about 25 to about 500° C. and a pressure of about 1 to about 100 kgf/cm² for about 1 to about 24 hrs. Specifically, the polymerization of the olefin-based monomer may be carried out at a temperature of about 25 to about 500° C., preferably about 25 to about 200° C., and more preferably about 50 to about 100° C. Furthermore, the reaction pressure may be about 1 to about 100 kgf/cm², preferably about 1 to about 50 kgf/cm², and more preferably about 5 to about 40 kgf/cm².

In the polyolefin prepared according to the present disclosure, specific examples of the olefin-based monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, etc., and it may be also a copolymer obtained by copolymerizing two or more thereof.

The polyolefin may be a polyethylene polymer, but is not limited thereto.

In the case where the polyolefin is an ethylene/alpha-olefin copolymer, a content of alpha-olefin as a comonomer is not particularly limited, and it may be adequately selected according to the use or purpose of the polyolefin. More specifically, the content may be more than 0 mole % and 99 mole % or less.

For example, the polyolefin prepared by using the metallocene supported catalyst of the present disclosure may exhibit a high molecular weight. When the polyolefin is prepared by using the supported catalyst, in which the metallocene compound is supported on the support, a high molecular weight polyolefin having a weight average molecular weight of about 100,000 g/mol or more, for example, about 100,000 to about 900,000 g/mol, or about 100,000 to about 600,000 g/mol may be prepared.

Further, the metallocene supported catalyst of the present disclosure exhibits an excellent activity, and the polyolefin prepared by using the metallocene supported catalyst of the present disclosure exhibits a wide molecular weight distribution (PDI) of about 2.0 to about 6.0, or about 3.0 to about 6.0, thereby showing excellent processability.

Further, according to an embodiment of the present disclosure, the polyolefin may have a density of about 0.85 to about 0.96 g/cm³, and preferably, about 0.90 to about 0.95 g/cm³.

Hereinafter, the preferred Examples are provided for better understanding. However, these Examples are for illustrative purposes only, and the invention is not intended to be limited by these Examples.

EXAMPLES

<Preparation of Metallocene Compound>

Preparation Example 1: Synthesis of ((1H-inden-2-yl)methyl)trimethylsilane

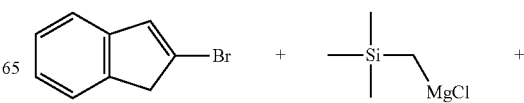

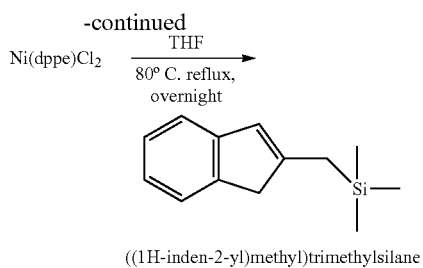

((1H-inden-2-yl)methyl)trimethylsilane 3.7 ml (30 mmol) of 2-Bromo-1H-indene was added to a flask, and Ar bubbling was performed for about 5 minutes while stirring in the presence of 100 ml of THF to remove dissolved gas. Under Ar bubbling, 0.8 g (1.5 mmol) of Ni(dppe)Cl$_2$ was rapidly added and 30 ml (30 mmol) of 1.0 M ((Trimethylsilyl)methyl)magnesium chloride dissolved in diethyl ether at room temperature was slowly added dropwise. And then, the reaction was continued overnight while refluxing under Ar condition at 80° C. (dppe=1,2-Bis(diphenylphosphino)ethane)

50 mL of water was added thereto, and the organic layer was extracted three times with 50 mL of diethylether. An appropriate amount of MgSO$_4$ was added to the collected organic layer, stirred for a while, filtered, and the solvent was dried under reduced pressure.

The resulting product was confirmed by $^1$H-NMR.

$^1$H-NMR (500 MHz, CDCl$_3$): 0.03 (9H, s), 3.25 (2H, s), 6.3 (1H, s), 7.02-7.32 (4H, m)

Example 1-1: Synthesis of Ligand Compound

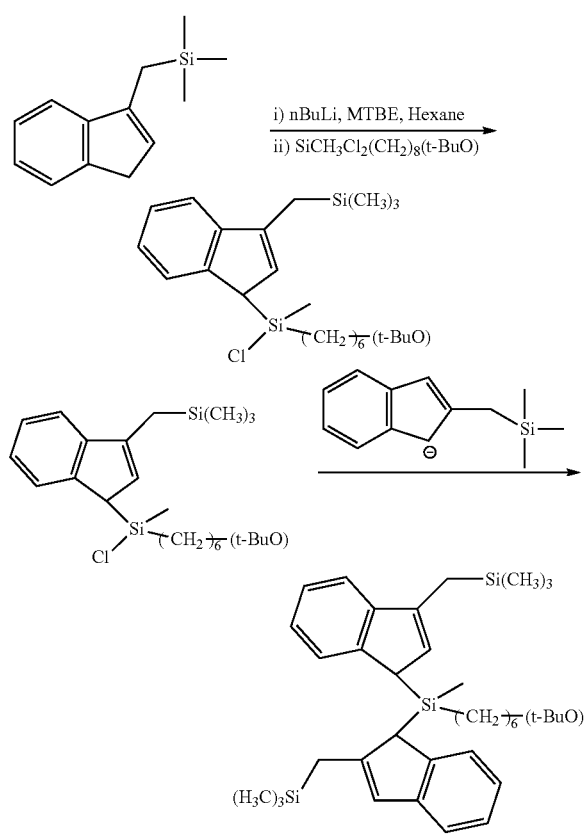

After dissolving 1.01 g (5 mmol) of ((1H-inden-3-yl)methyl)trimethylsilane in 80 ml of Hexane and 2.4 ml of MTBE, 2.4 mL (6 mmol) of a 2.50 M n-BuLi hexane solution was added thereto dropwise in a dry ice/acetone bath. The reaction mixture was slowly warmed up to room temperature, and then stirred for 24 hours, followed by addition of 50 ml of Hexane.

Another 250 mL Schlenk flask was placed in the glove box and weighed 1.36 g (5 mmol) of SiCH$_3$Cl$_2$(CH$_2$)$_6$(t-BuO) in the glove box. And it was taken out of the glove box, dissolved in 50 mL of Hexane, and then the mixture prepared above was added thereto dropwise in a dry ice/acetone bath (Synthesized Compound 1-1).

Separately, after dissolving 1.01 g (5 mmol) of ((1H-inden-2-yl)methyl)trimethylsilane of the Preparation Example 1 in 50 ml of THF, 2.4 mL (6 mmol) of a 2.50 M n-BuLi Hexane solution was added thereto dropwise in a dry ice/acetone bath. The reaction mixture was slowly warmed up to room temperature, and then stirred for 24 hours, followed by addition of 50 ml of Hexane (Synthesized Compound 1-2).

After the Synthesized Composition 1-2 was added to the Synthesized Composition 1-1 dropwise in a dry ice/acetone bath, the reaction mixture was slowly warmed up to room temperature, and then stirred for 24 hours.

50 mL of water was added thereto, and the organic layer was extracted three times with 50 mL of ether. An appropriate amount of MgSO$_4$ was added to the collected organic layer, stirred for a while, filtered, and the solvent was dried under reduced pressure to obtain 3.02 g (5 mmol) of a ligand compound in an oil phase, which was confirmed by $^1$H-NMR.

The obtained ligand compound was used for the preparation of the metallocene compound.

$^1$H NMR (500 MHz, CDCl$_3$): −0.38 (3H, s), 0.02 (18H, s), 1.17 (9H, m), 1.16 (9H, s), 0.41-1.52 (10H, m), 1.96 (2H, s), 2.04 (2H, m), 2.4 (1H, m), 3.23 (2H, m), 3.5 (1H, m), 6.02 (1H, m), 6.30 (1H, m), 7.0-7.46 (8H, m)

Example 1-2: Synthesis of Metallocene Compound

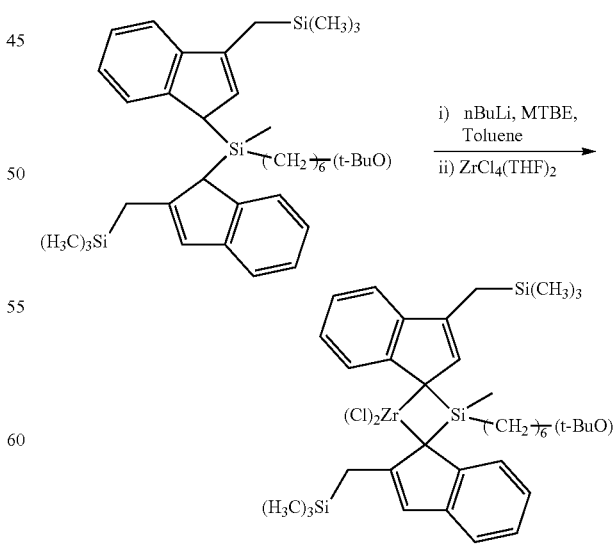

After dissolving 3.02 g (4.7 mmol) of the ligand compound synthesized in Example 1-1 in 80 mL of toluene and 2.6 mL of MTBE in a 250 mL Schlenk flask which is dried in an oven, 4.4 mL (11 mmol) of a 2.5 M n-BuLi Hexane solution was added thereto dropwise in a dry ice/acetone bath. The reaction mixture was slowly warmed up to room temperature, and then stirred for 24 hours, followed by lithiation.

1.88 g (5 mmol) of $ZrCl_4(THF)_2$ was taken in a glove box and injected into another 250 mL Schlenk flask to prepare a suspension having 80 mL of toluene. The above two flasks were cooled down to −78° C. and the lithiated ligand compound was slowly added to the toluene suspension of $ZrCl_4(THF)_2$. After the completion of the injection, the reaction mixture was slowly warmed up to room temperature, stirred for one day and subjected to reaction. Then, toluene in the mixture was removed up to a volume of about 1/5 through vacuum-reduced pressure. Hexane was added in about 5 times volume of the remaining toluene thereto and recrystallized. The mixture was filtered without contacting with the outside air to give a metallocene compound. The resulting filter cake in the upper portion of the filter was washed using a little Hexane, and then weighed in the glove box to identify the synthesis and yield (yield: 97%).

The resulting product was stored in a toluene solution.

$^1$H NMR (500 MHz, $CDCl_3$): −0.1 (18H, m), 1.17 (9H, m), 1.49 (3H, s), 0.84-2.21 (10H, m), 1.84 (2H, s), 2.34 (2H, s), 3.32 (2H, m), 5.62 (2H, d), 6.5-7.6 (8H, m)

Example 2-1: Synthesis of Ligand Compound

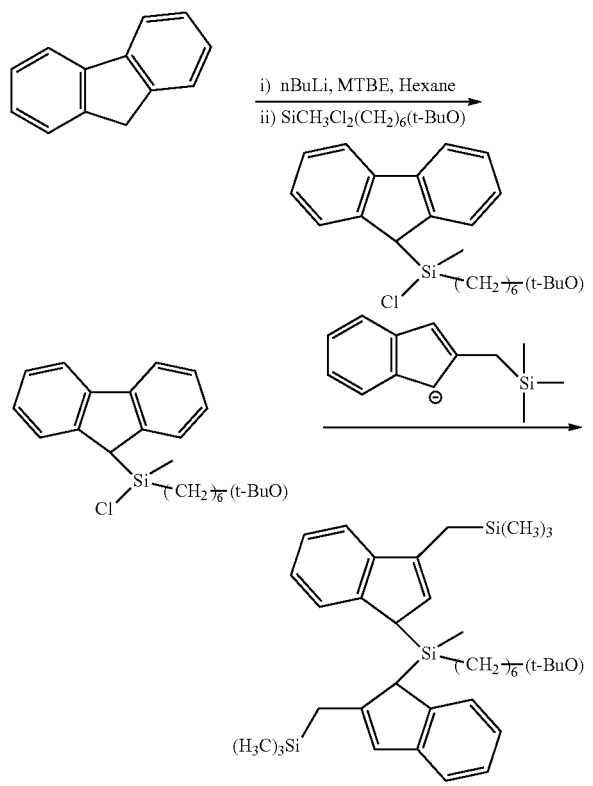

After dissolving 1 g (6 mmol) of fluorene in 60 ml of Hexane and 2.4 ml of MTBE, 2.9 mL (7.2 mmol) of a 2.50 M n-BuLi Hexane solution was added thereto dropwise in a dry ice/acetone bath. The reaction mixture was slowly warmed up to room temperature, and then stirred for 24 hours.

Another 250 mL Schlenk flask was placed in the glove box and weighed 1.62 g (6 mmol) of $SiCH_3Cl_2(CH_2)_6(t-BuO)$ in the glove box. And it was taken out of the glove box, dissolved in 50 mL of Hexane, and then the mixture prepared above was added thereto dropwise in a dry ice/acetone bath (Synthesized Compound 2-1).

Separately, after dissolving 1.21 g (6 mmol) of ((1H-inden-2-yl)methyl)trimethylsilane of the Preparation Example 1 in 80 ml of THF, 2.9 mL (7.2 mmol) of a 2.50 M n-BuLi Hexane solution was added thereto dropwise in a dry ice/acetone bath. The reaction mixture was slowly warmed up to room temperature, and then stirred for 24 hours. And, a portion was sampled, dried, and then sampled for NMR in a glove box to identify the progress and completion of the reaction (Synthesized Compound 2-2).

$^1$H NMR (500 MHz, $C_6D_6$): −0.01 (3H, s), 1.12 (9H, m), 1.03-1.46 (10H, m), 3.17 (2H, t), 3.87 (1H, s), 7.15-7.78 (8H, m)

After the Synthesized Composition 2-2 was added to the Synthesized Composition 2-1 dropwise in a dry ice/acetone bath, the reaction mixture was slowly warmed up to room temperature, and then stirred for 24 hours.

50 mL of water was added thereto, and the organic layer was extracted three times with 50 mL of ether. An appropriate amount of $MgSO_4$ was added to the collected organic layer, stirred for a while, filtered, and the solvent was dried under reduced pressure to obtain 3.36 g (5.9 mmol) of a ligand compound in an oil phase, which was confirmed by $^1$H-NMR.

The obtained ligand compound was used for the preparation of the metallocene compound.

$^1$H NMR (500 MHz, $CDCl_3$): −0.01 (3H, d), 1.16 (9H, m), 0.79-1.31 (10H, m), 1.57 (2H, s), 1.96 (1H, s), 3.25 (2H, m), 4.08 (1H, s), 6.34 (1H, d), 7.03-7.87 (12H, m)

Example 2-2: Synthesis of Metallocene Compound

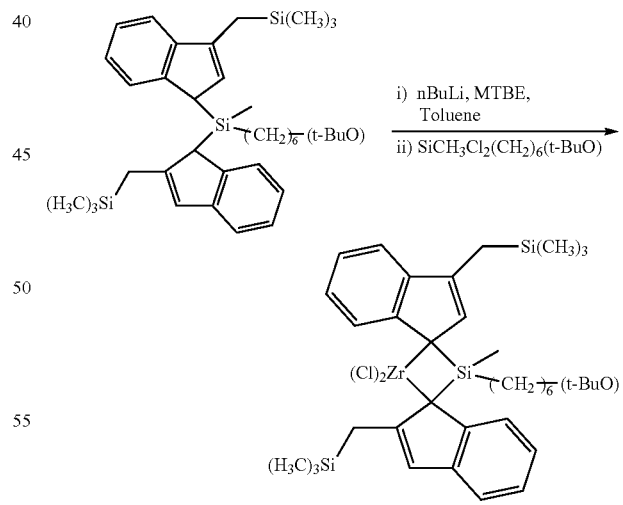

After dissolving 3.36 g (5.9 mmol) of the ligand compound synthesized in Example 2-1 in 80 mL of toluene and 2.6 mL of MTBE in a 250 mL Schlenk flask which is dried in an oven, 5.2 mL (13 mmol) of a 2.5 M n-BuLi Hexane solution was added thereto dropwise in a dry ice/acetone bath. The reaction mixture was slowly warmed up to room temperature, and then stirred for 24 hours, followed by lithiation.

2.23 g (5.9 mmol) of ZrCl$_4$(THF)$_2$ was taken in a glove box and injected into another 250 mL Schlenk flask to prepare a suspension having 80 mL of toluene. The above two flasks were cooled down to −78° C. and the lithiated ligand compound was slowly added to the toluene suspension of ZrCl$_4$(THF)$_2$. After the completion of the injection, the reaction mixture was slowly warmed up to room temperature, stirred for one day and subjected to reaction. Then, toluene in the mixture was removed up to a volume of about ⅕ through vacuum-reduced pressure. Hexane was added in about 5 times volume of the remaining toluene thereto and recrystallized. The mixture was filtered without contacting with the outside air to give a metallocene compound in a brown powder phase. The resulting filter cake in the upper portion of the filter was washed using a little Hexane, and then weighed in the glove box to identify the synthesis and yield (yield: 82%).

$^1$H NMR (500 MHz, CDCl$_3$): −0.15 (9H, s), 1.3 (9H, m), 1.8 (3H, m), 0.9-1.8 (10H, m), 2.3 (2H, d), 3.4 (2H, m), 5.6 (1H, s), 6.5-8.0 (12H, m)

Example 3-1: Synthesis of Ligand Compound

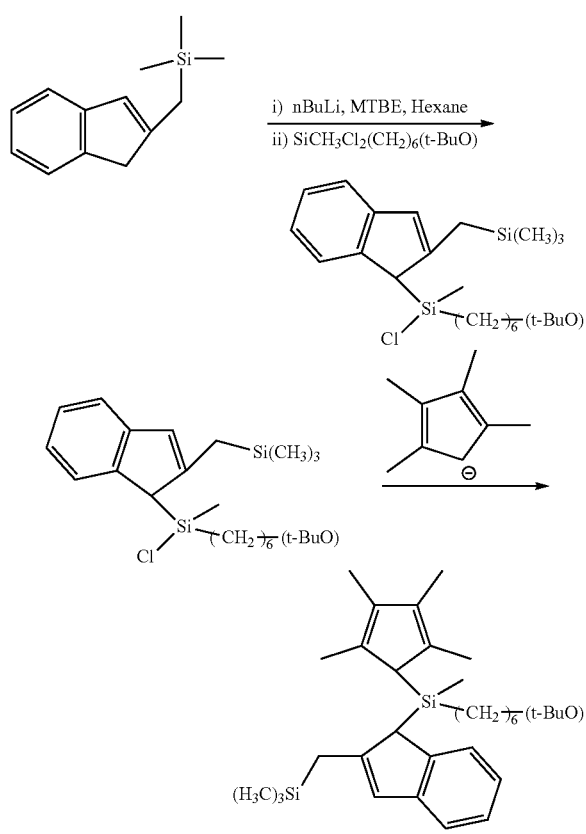

After dissolving 1.01 g (5 mmol) of ((1H-inden-2-yl) methyl)trimethylsilane of the Preparation Example 1 in 80 ml of THF, 2.4 mL (6 mmol) of a 2.50 M n-BuLi Hexane solution was added thereto dropwise in a dry ice/acetone bath. The reaction mixture was slowly warmed up to room temperature, and then stirred for 24 hours, followed by addition of 50 ml of Hexane.

In another 250 mL Schlenk flask was placed in the glove box and weighed 1.36 g (5 mmol) of SiCH$_3$Cl$_2$(CH$_2$)$_6$(t-BuO) in the glove box. And it was taken out of the glove box, dissolved in 50 mL of Hexane, and then the mixture prepared above was added thereto dropwise in a dry ice/acetone bath (Synthesized Compound 3-1).

Separately, after dissolving 0.61 g (5 mmol) of 1,2,3,4-tetramethylcyclopenta-1,3-diene in 80 ml of THF, 2.4 mL (6 mmol) of a 2.50 M n-BuLi Hexane solution was added thereto dropwise in a dry ice/acetone bath. The reaction mixture was slowly warmed up to room temperature, and then stirred for 24 hours (Synthesized Compound 3-2).

After the Synthesized Composition 3-2 was added to the Synthesized Composition 3-1 dropwise in a dry ice/acetone bath, the reaction mixture was slowly warmed up to room temperature, and then stirred for 24 hours.

50 mL of water was added thereto, and the organic layer was extracted three times with 50 mL of ether. An appropriate amount of MgSO$_4$ was added to the collected organic layer, stirred for a while, filtered, and the solvent was dried under reduced pressure to obtain 2.07 g (3.96 mmol) of a ligand compound in an oil phase, which was confirmed by $^1$H-NMR.

The obtained ligand compound was used for the preparation of the metallocene compound.

$^1$HNMR (500 MHz, CDCl$_3$): −0.21 (3H, s), −0.01 (9H, m), 0.04 (12H, m), 1.16 (9H, m), 0.9-1.54 (10H, m), 2.09 (2H, d), 3.30 (2H, m), 4.19 (1H, d), 4.52 (1H, d), 6.41 (1H, m), 7.0-7.33 (4H, m)

Example 3-2: Synthesis of Metallocene Compound

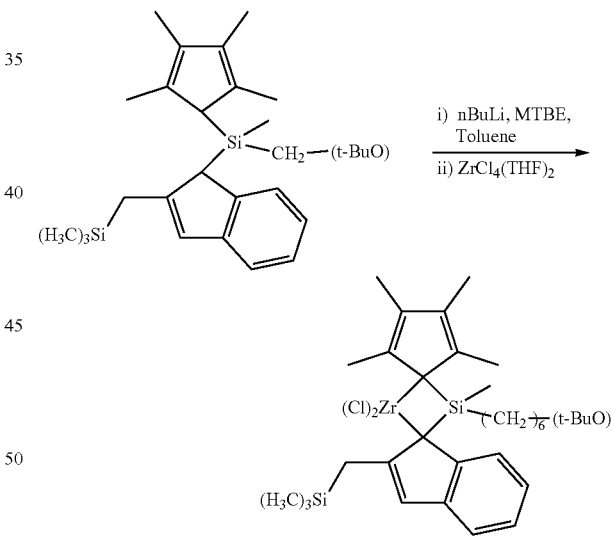

After dissolving 2.07 g (3.96 mmol) of the ligand compound synthesized in Example 3-1 in 80 mL of toluene and 2.6 mL of MTBE in a 250 mL Schlenk flask which is dried in an oven, 3.5 mL (8.7 mmol) of a 2.5 M n-BuLi Hexane solution was added thereto dropwise in a dry ice/acetone bath. The reaction mixture was slowly warmed up to room temperature, and then stirred for 24 hours, followed by lithiation.

1.49 g (3.96 mmol) of ZrCl$_4$(THF)$_2$ was taken in a glove box and injected into another 250 mL Schlenk flask to prepare a suspension having 80 mL of toluene. The above two flasks were cooled down to −78° C. and the lithiated ligand compound was slowly added to the toluene suspension of ZrCl$_4$(THF)$_2$. After the completion of the injection, the reaction mixture was slowly warmed up to room temperature, stirred for one day and subjected to reaction. Then, toluene in the mixture was removed up to a volume of about ⅕ through vacuum-reduced pressure. Hexane was added in about 5 times volume of the remaining toluene thereto and recrystallized. The mixture was filtered without contacting with the outside air to give a metallocene compound. The resulting filter cake in the upper portion of the filter was washed using a little Hexane, and then weighed in the glove box to identify the synthesis and yield (yield: 70%).

The resulting product was stored in a toluene solution.

$^1$H NMR (500 MHz, CDCl$_3$): −0.32 (3H, s), 0.01 (12H, s), 0.07 (9H, s), 1.16 (9H, s), 0.8-1.5 (10H, m), 1.38 (2H, s), 3.23 (2H, s), 4.19 (1H, d), 4.5 (1H, d), 6.4 (2H, m), 6.96-7.33 (4H, m)

Example 4-1: Synthesis of Ligand Compound

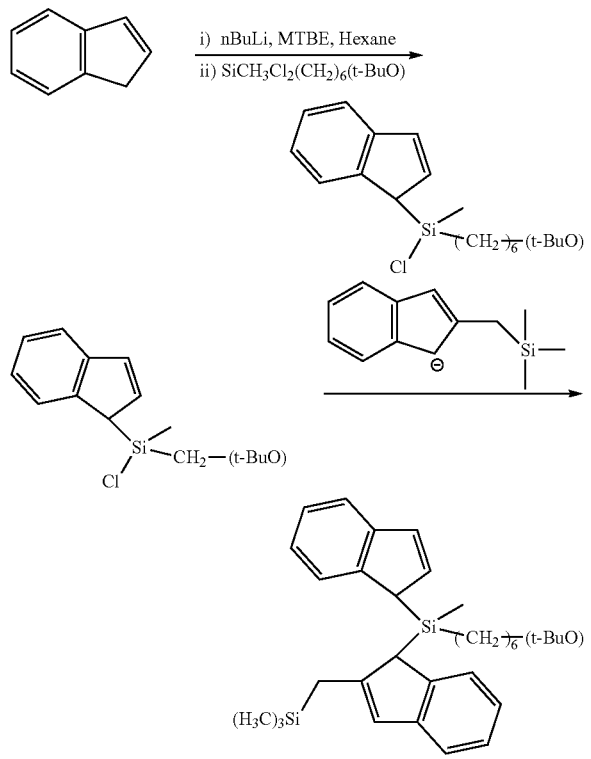

After dissolving 0.58 g (5 mmol) of Indene in 100 ml of Hexane and 3.0 ml of MTBE, 2.4 mL (6 mmol) of a 2.50 M n-BuLi Hexane solution was added thereto dropwise in a dry ice/acetone bath. The reaction mixture was slowly warmed up to room temperature, and then stirred for 24 hours.

Another 250 mL Schlenk flask was placed in the glove box and weighed 1.36 g (5 mmol) of SiCH$_3$Cl$_2$(CH$_2$)$_6$(t-BuO) in the glove box. And it was taken out of the glove box, dissolved in 100 mL of Hexane, and then the mixture prepared above was added thereto dropwise in a dry ice/acetone bath (Synthesized Compound 4-1).

Separately, after dissolving 1.01 g (5 mmol) of ((1H-inden-2-yl)methyl)trimethylsilane of the Preparation Example 1 in 100 ml of THF, 2.4 mL (6 mmol) of a 2.50 M n-BuLi Hexane solution was added thereto dropwise in a dry ice/acetone bath. The reaction mixture was slowly warmed up to room temperature, and then stirred for 24 hours. And, a portion was sampled, dried, and then sampled for NMR in a glove box to identify the progress and completion of the reaction (Synthesized Compound 4-2).

After the Synthesized Composition 4-2 was added to the Synthesized Composition 4-1 dropwise in a dry ice/acetone bath, the reaction mixture was slowly warmed up to room temperature, and then stirred for 24 hours.

50 mL of water was added thereto, and the organic layer was extracted three times with 50 mL of ether. An appropriate amount of MgSO$_4$ was added to the collected organic layer, stirred for a while, filtered, and the solvent was dried under reduced pressure to obtain 2.6 g (5 mmol) of a ligand compound in an oil phase, which was confirmed by $^1$H-NMR.

The obtained ligand compound was used for the preparation of the metallocene compound.

$^1$H NMR (500 MHz, CDCl$_3$): −0.04 (3H, d), 0.04 (9H, s), 1.1 (9H, s), 0.8-1.8 (20H, m), 2.02 (2H, s), 2.15 (1H, s), 3.05 (1H, s), 3.26 (1H, s), 3.57 (2H, m), 6.2-6.36 (3H, m), 7.03-7.46 (8H, m)

Example 4-2: Synthesis of Metallocene Compound

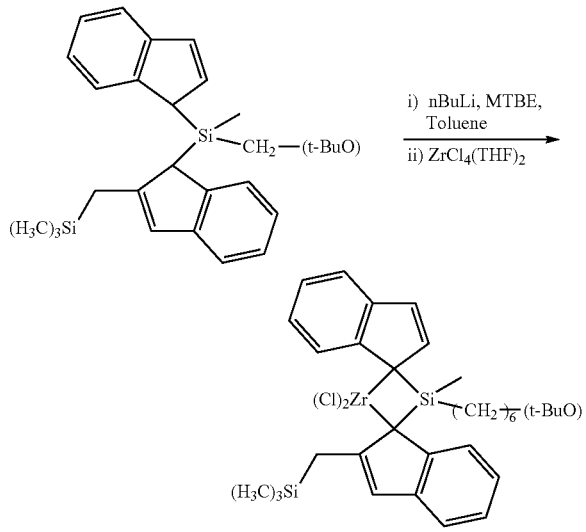

After dissolving 2.6 g (5 mmol) of the ligand compound synthesized in Example 4-1 in 100 mL of toluene and 3 mL of MTBE in a 250 mL Schlenk flask which is dried in an oven, 4.8 mL (12 mmol) of a 2.5 M n-BuLi Hexane solution was added thereto dropwise in a dry ice/acetone bath. The reaction mixture was slowly warmed up to room temperature, and then stirred for 24 hours, followed by lithiation.

1.88 g (5 mmol) of ZrCl$_4$(THF)$_2$ was taken in a glove box and injected into another 250 mL Schlenk flask to prepare a suspension having 100 mL of toluene. The above two flasks were cooled down to −78° C. and the lithiated ligand compound was slowly added to the toluene suspension of ZrCl$_4$(THF)$_2$. After the completion of the injection, the reaction mixture was slowly warmed up to room temperature, stirred for one day and subjected to reaction. Then, toluene in the mixture was removed up to a volume of about ⅕ through vacuum-reduced pressure. Hexane was added in about 5 times volume of the remaining toluene thereto and recrystallized. The mixture was filtered without contacting with the outside air to give a metallocene compound in a dark red powder phase. The resulting filter cake in the upper portion of the filter was washed using a little Hexane, and then weighed in the glove box to identify the synthesis.

$^1$H NMR (500 MHz, CDCl$_3$): −0.1 (9H, m), 1.12 (9H, m), 1.23 (3H, s), 0.8-1.8 (19H, m), 1.93 (2H, s), 2.1 (1H, s), 3.3 (2H, m), 6.25-6.8 (3H, m), 6.9-7.6 (8H, m)

Example 5-1: Synthesis of Ligand Compound

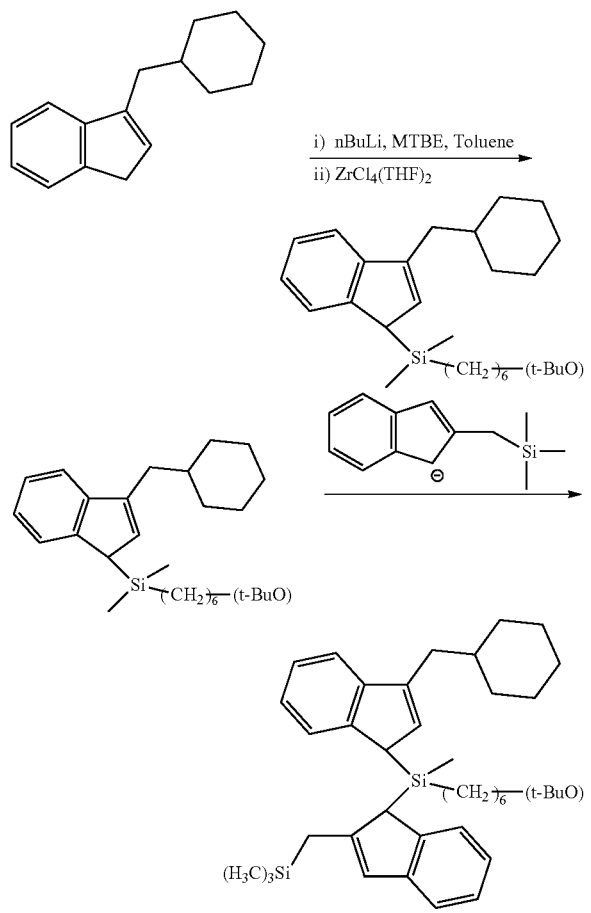

After dissolving 1.06 g (5 mmol) of 3-(cyclohexylmethyl)-1H-indene in 50 ml of Hexane and 2.4 ml of MTBE, 2.4 mL (6 mmol) of a 2.50 M n-BuLi Hexane solution was added thereto dropwise in a dry ice/acetone bath. The reaction mixture was slowly warmed up to room temperature, and then stirred for 24 hours.

Another 250 mL Schlenk flask was placed in the glove box and weighed 1.36 g (5 mmol) of SiCH$_3$Cl$_2$(CH$_2$)$_6$(t-BuO) in the glove box. And it was taken out of the glove box, dissolved in 100 mL of Hexane, and then the mixture prepared above was added thereto dropwise in a dry ice/acetone bath (Synthesized Compound 5-1).

Separately, after dissolving 1.01 g (5 mmol) of ((1H-inden-2-yl)methyl)trimethylsilane of the Preparation Example 1 in 80 ml of THF, 2.4 mL (6 mmol) of a 2.50 M n-BuLi Hexane solution was added thereto dropwise in a dry ice/acetone bath. The reaction mixture was slowly warmed up to room temperature, and then stirred for 24 hours (Synthesized Compound 5-2).

After the Synthesized Composition 5-2 was added to the Synthesized Composition 5-1 dropwise in a dry ice/acetone bath, the reaction mixture was slowly warmed up to room temperature, and then stirred for 24 hours.

50 mL of water was added thereto, and the organic layer was extracted three times with 50 mL of ether. An appropriate amount of MgSO$_4$ was added to the collected organic layer, stirred for a while, filtered, and the solvent was dried under reduced pressure to obtain 3.03 g (4.96 mmol) of a ligand compound in an oil phase, which was confirmed by $^1$H-NMR.

The obtained ligand compound was used for the preparation of the metallocene compound.

$^1$H NMR (500 MHz, CDCl$_3$): −0.01 (3H, d), 0.04 (9H, s), 1.2 (9H, s), 0.8-1.8 (20H, m), 1.96 (2H, s), 3.26 (2H, s), 3.46 (1H, m), 3.57 (1H, m), 6.3 (1H, s), 6.43 (1H, s), 7.03-7.46 (8H, m)

Example 5-2: Synthesis of Metallocene Compound

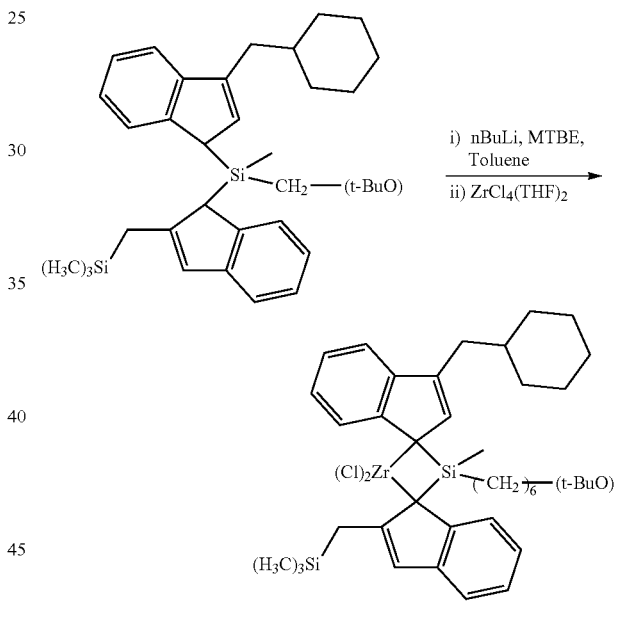

After dissolving 3.03 g (4.94 mmol) of the ligand compound synthesized in Example 5-1 in 80 mL of toluene and 2.6 mL of MTBE in a 250 mL Schlenk flask which is dried in an oven, 4.4 mL (10.8 mmol) of a 2.5 M n-BuLi Hexane solution was added thereto dropwise in a dry ice/acetone bath. The reaction mixture was slowly warmed up to room temperature, and then stirred for 24 hours, followed by lithiation.

1.86 g (4.94 mmol) of ZrCl$_4$(THF)$_2$ was taken in a glove box and injected into another 250 mL Schlenk flask to prepare a suspension having 100 mL of toluene. The above two flasks were cooled down to −78° C. and the lithiated ligand compound was slowly added to the toluene suspension of ZrCl$_4$(THF)$_2$. After the completion of the injection, the reaction mixture was slowly warmed up to room temperature, stirred for one day and subjected to reaction. Then, toluene in the mixture was removed up to a volume of about ⅕ through vacuum-reduced pressure. Hexane was added in about 5 times volume of the remaining toluene thereto and recrystallized. The mixture was filtered without contacting with the outside air to give a metallocene compound in a brown solid phase. The resulting filter cake in the upper portion of the filter was washed using a little Hexane, and then weighed in the glove box to identify the synthesis (yield: 66%).

$^1$H NMR (500 MHz, CDCl$_3$): −0.14 (9H, s), −0.03 (3H, d), 1.15 (9H, s), 0.47-1.58 (20H, m), 1.48 (2H, s), 1.84 (2H, s), 3.33 (2H, m), 3.57 (1H, m), 5.62 (2H, s), 6.8-7.6 (8H, m)

<Preparation of Supported Catalyst>

Example 1-3

100 ml of toluene was introduced to a 300 ml bench scale reactor, and 10 g of silica (SP952X manufactured by Grace Davison, used after sintering at 650° C.) was added thereto at 40° C., followed by stirring at 500 rpm for 30 minutes. 10 wt % of MAO solution was added thereto so that the amount of MAO solution was 8 mmol/g with respect to the weight of the silica, the temperature was warmed up to 60° C., and the reaction was carried out under stirring at 500 rpm for 16 hours. The reactor temperature was cooled down to 40° C., stirring was stopped, stabilized for 10 minutes, and the liquid at the top was discharged by decantation.

Toluene was added thereto until the reactor scale reached 100 ml, and the metallocene compound prepared in Example 1-2 was added thereto so that the amount of the metallocene compound was 0.1 mmol/g with respect to the weight of silica, and the mixture was reacted for 1.5 hours under stirring at 500 rpm. The reactor temperature was cooled down to room temperature, stirring was stopped, stabilized for 10 minutes, and the liquid at the top was discharged by decantation.

Toluene was added thereto again until the reactor scale reached 100 ml, and 10 minutes of stirring, 10 minutes of stabilization and decantation were repeated.

Hexane was added thereto until the reactor scale reached 100 ml, ASA (Alkylamine ethoxylate, product name: Atmer 163) was added in an amount of 2% by weight based on the weight of silica as an antistatic agent, and the mixture was stirred for 10 minutes. The resulting slurry was transferred to a flask, and then dried under reduced pressure for 3 hours to prepare a metallocene supported catalyst in the form of a solid powder.

Example 2-3 to 5-3

A metallocene supported catalyst was prepared in the same manner as in Example 1-3, except that the metallocene compounds of Examples 2-2 to 5-2 were used instead of the metallocene compounds of Example 1-2.

Examples of Olefin Polymerization

Polymerization of Ethylene

Example 1-4

About 10 mg of the supported catalyst prepared in Example 1-3 was weighed in a dry box, introduced to a 50 mL glass bottle together with hexane to block the contact with air, and sealed with a rubber diaphragm. And then, a catalyst to be injected was taken from the dry box and prepared.

Polymerization was carried out in a 600 mL metal alloy reactor which can control the temperature and can be used at high pressure equipped with a mechanical stirrer.

0.46 g of triethylaluminum and 0.16 ml of ASA were added into the reactor, and 0.24 kg of hexane was added thereto. Then, the temperature of the reactor was warmed up to 80° C. while stirring at 500 rpm.

The prepared supported catalyst was added with hexane to the reactor and stirred at 100 rpm while maintaining the temperature at 80° C.

Ethylene was injected under a pressure of 30 bar and the reaction was conducted for 1 hour while stirring at 500 rpm. The polymerization was terminated by stopping the stirring first and then removing unreacted ethylene.

The resulting polymer was filtered to remove most of the polymer solvent, and then dried in a vacuum oven at 80° C. for 4 hours.

Examples 2-4 to 5-4

The polymerization was carried out in the same manner as in Example 1-4, except that the supported catalysts of Examples 2-3 to 5-3 were used instead of the supported catalyst of Example 1-3.

Supporting conditions of the respective catalysts prepared above, catalytic activities thereof, physical properties of the resulting polymers, etc. are shown in the following Table 1.

TABLE 1

| Example No. | Supported catalyst | Supporting Recipe | | Activity Kg(PE)/g(Cat) | MW (10$^4$ g/mol) |
|---|---|---|---|---|---|
| | | MAO (60° C.) mmol/g (SiO$_2$) | Met (40° C.) mmol/g (SiO$_2$) | | |
| Example 1-4 | Example 1-3 | 8 | 0.1 | 2.6 | 38.0 |
| Example 2-4 | Example 2-3 | 8 | 0.1 | 2.8 | 70.0 |
| Example 3-4 | Example 3-3 | 8 | 0.1 | 5.8 | 18.0 |
| Example 4-4 | Example 4-3 | 8 | 0.1 | 3.2 | 23.0 |
| Example 5-4 | Example 5-3 | 8 | 0.1 | 6.2 | 28.0 |

Referring to Table 1, the metallocene supported catalyst of the present disclosure maintains high activity during olefin polymerization, even when it is supported on a support, and is able to prepare a polyolefin having a high molecular weight.

The invention claimed is:
1. A metallocene supported catalyst, comprising a metallocene compound represented by the following Chemical Formula 1;
a cocatalyst compound; and
a support:

[Chemical Formula 1]

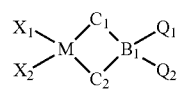

wherein in Chemical Formula 1,
M is a Group 4 transition metal;
B$_1$ is carbon, silicon, or germanium;
Q$_1$ and Q$_2$ are the same as or different from each other, and are each independently hydrogen, halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

$X_1$ and $X_2$ are the same as or different from each other, and are each independently halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group;

$C_1$ is represented by the following Chemical Formula 2a, and $C_2$ is represented by the following Chemical Formula 2b or Chemical Formula 2c;

[Chemical Formula 2a]

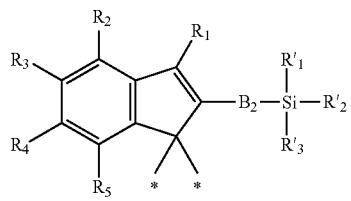

[Chemical Formula 2b]

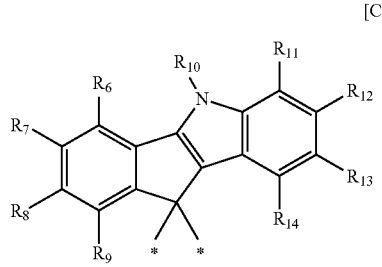

[Chemical Formula 2c]

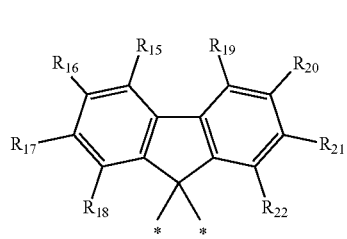

wherein, in Chemical Formulae 2a, 2b and 2c, $B_2$ is a single bond or a C1 to C3 alkylene group,

* is a site to which M or $B_1$ of Chemical Formula 1 is connected, $R_1$ to $R_5$ are the same as or different from each other, and are each independently hydrogen, halogen, a C1 to C20 alkyl group, a C2 to C20 alkenyl group, an C1 to C20 ether group, a C1 to C20 alkoxy group, a C6 to C20 aryl group, a C7 to C20 alkylaryl group, or a C7 to C20 arylalkyl group, $R_6$ to $R_{22}$ are the same as or different from each other, and are each independently hydrogen, halogen, a C1 to C20 alkyl group, a C1 to C20 alkoxy group, a C6 to C20 aryl group, a C7 to C20 alkylaryl group, or a C7 to C20 arylalkyl group, $R'_1$ to $R'_3$ are the same as or different from each other, and are each independently hydrogen, halogen, or a C1 to C20 alkyl group.

2. The metallocene supported catalyst of claim 1, wherein $R_1$ to $R_5$ in the Chemical Formulae 2a, 2b and 2c are each independently hydrogen, halogen, a methyl group, an ethyl group, a propyl group, an isopropyl group, an n-butyl group, a tert-butyl group, a pentyl group, a hexyl group, a heptyl group, an octyl group, an ethylene group, a propylene group, a butylene group, a phenyl group, a benzyl group, a naphthyl group, a halogen group, an ether group, a dimethyl ether group, a methoxy group, an ethoxy group, or a tert-butoxyhexyl group, and $R_6$ to $R_{22}$ are each independently hydrogen, halogen, a methyl group, an ethyl group, a propyl group, an isopropyl group, an n-butyl group, a tert-butyl group, a pentyl group, a hexyl group, a heptyl group, an octyl group, an ethylene group, a propylene group, a butylene group, a phenyl group, a benzyl group, a naphthyl group, a halogen group, an ether group, a trimethylsilyl group, a triethylsilyl group, a tripropylsilyl group, a tributylsilyl group, a triisopropylsilyl group, a trimethylsilylmethyl group, a dimethyl ether group, tert-butyldimethylsilyl ether group, a methoxy group, an ethoxy group, or a tert-butoxyhexyl group.

3. The metallocene supported catalyst of claim 1, wherein $Q_1$ and $Q_2$ in the Chemical Formula 1 are each independently hydrogen, a methyl group, an ethyl group, a propyl group, an isopropyl group, an n-butyl group, a tert-butyl group, a methoxymethyl group, a tert-butoxymethyl group, a 1-ethoxyethyl group, a 1-methyl-1-methoxyethyl group, a tert-butoxyhexyl group, a tetrahydropyranyl group, or a tetrahydrofuranyl group.

4. The metallocene supported catalyst of claim 1, wherein the compound represented by the Chemical Formula 2a is any one of the following structural formulae:

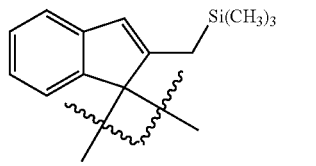

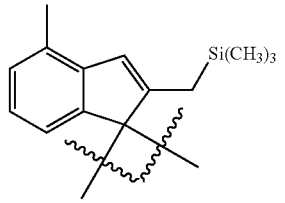

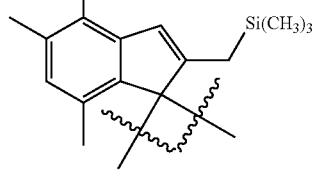

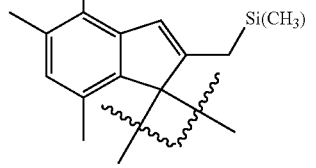

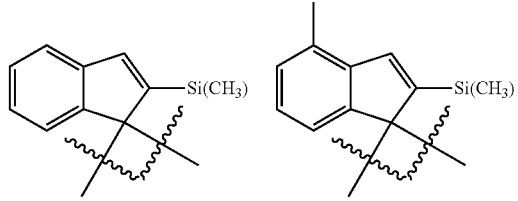

-continued
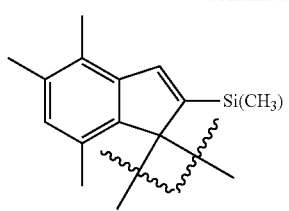
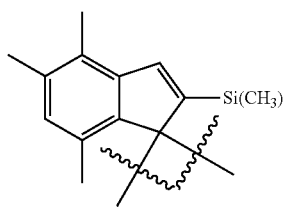
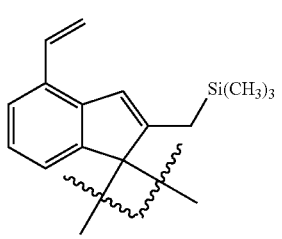
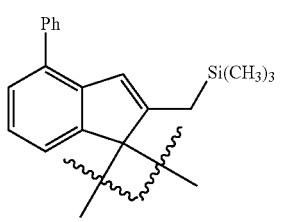
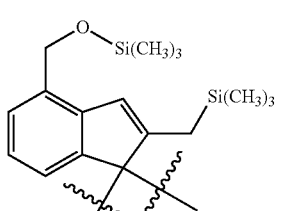
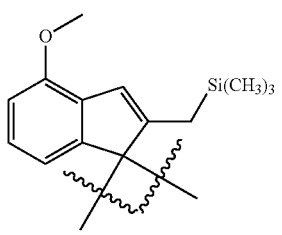
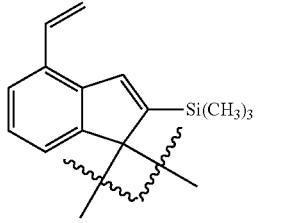
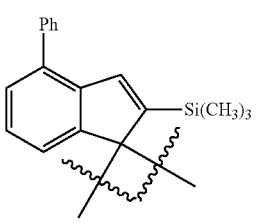
-continued
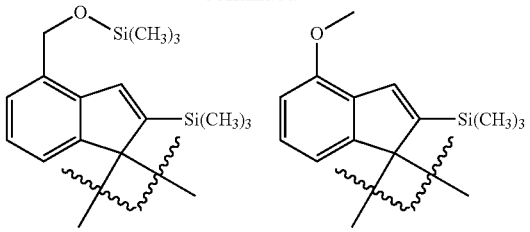
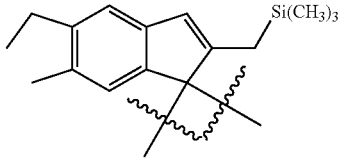
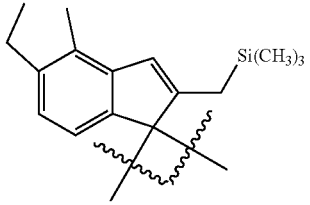
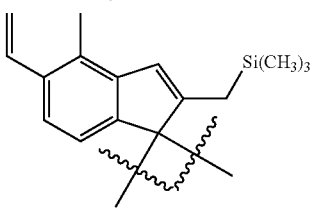
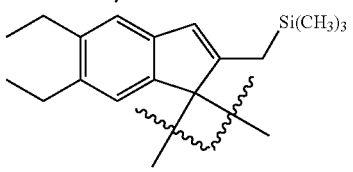
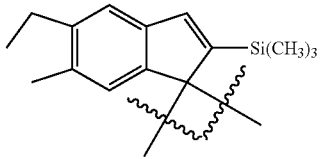
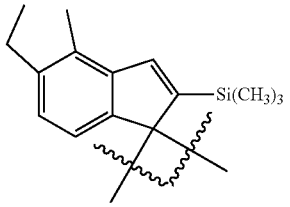
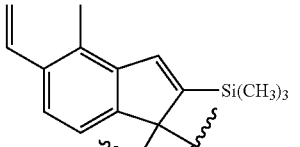
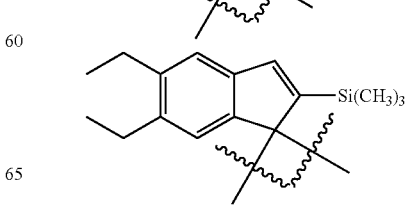

-continued
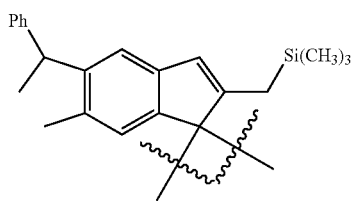
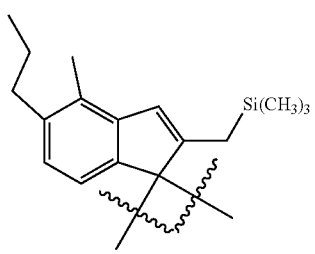
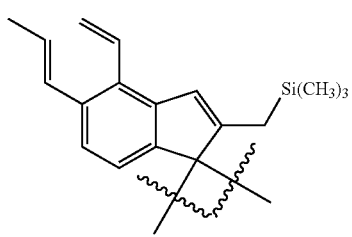
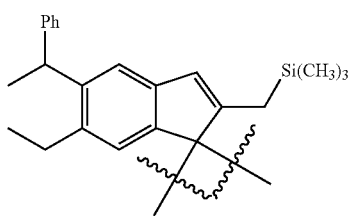
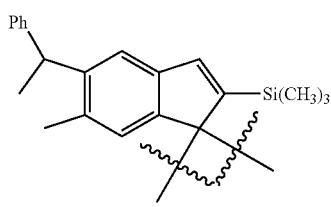
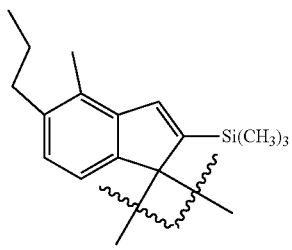
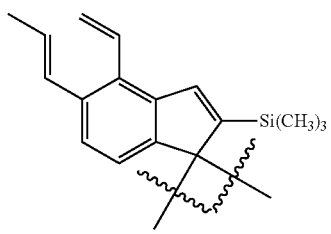
-continued
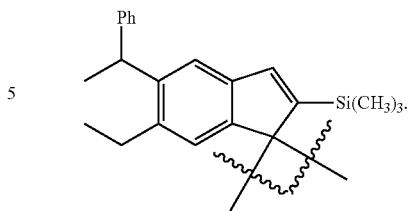
5. The metallocene supported catalyst of claim 1, wherein the compound represented by the Chemical Formula 2b is any one of the following structural formulae:
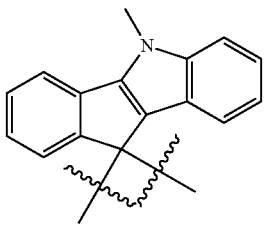
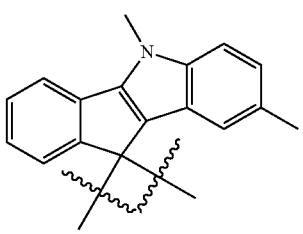
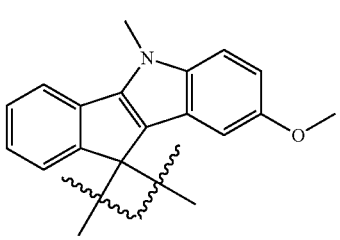
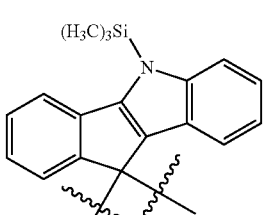
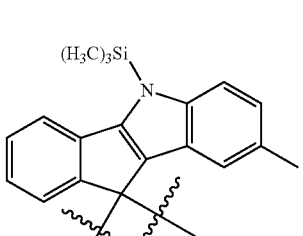

-continued
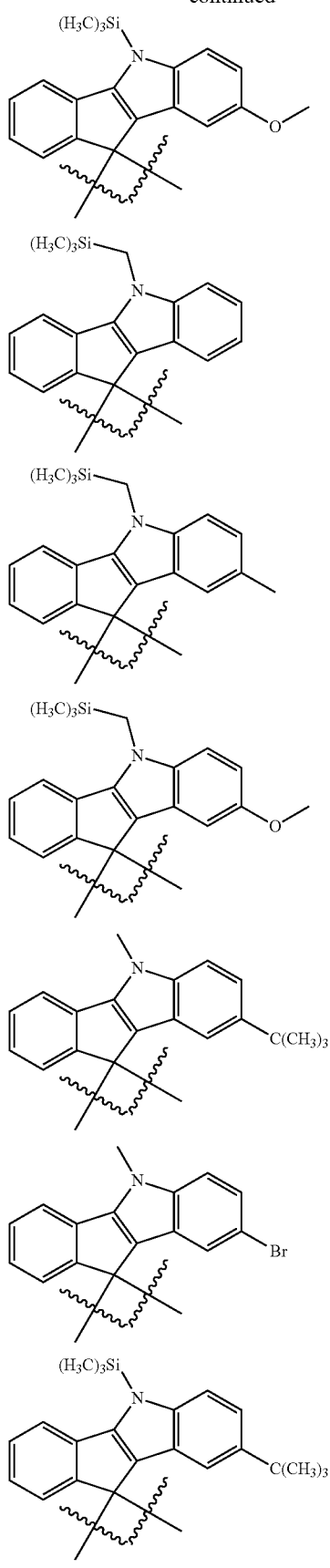
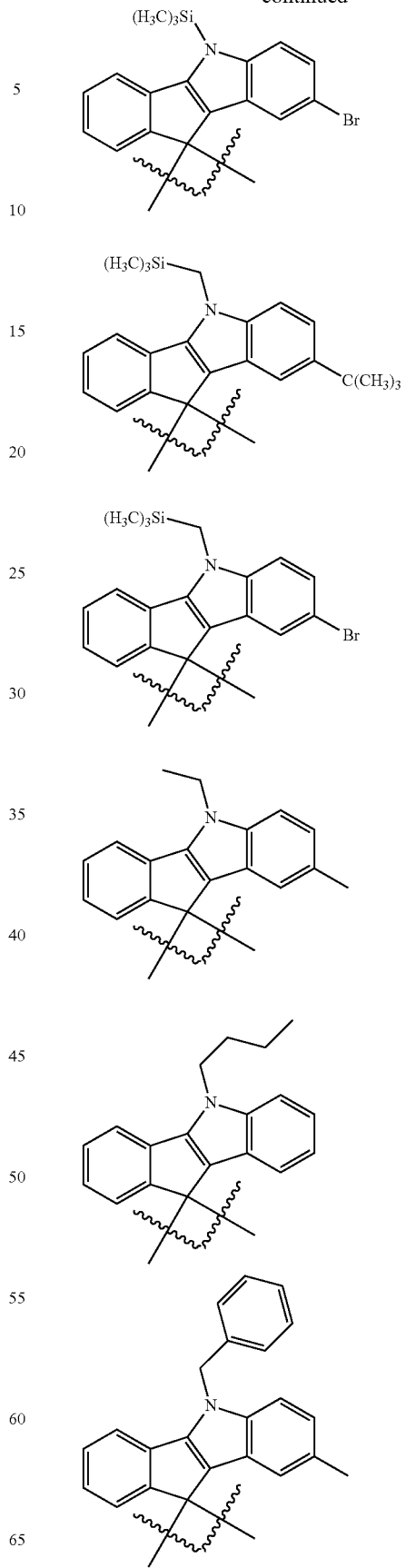

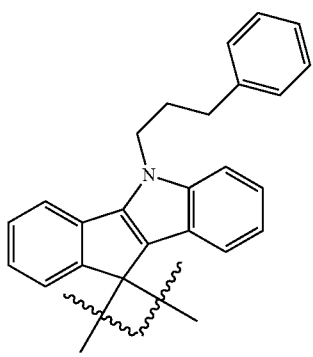
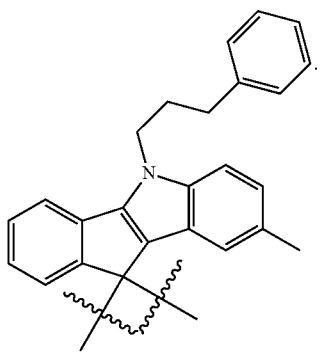
6. The metallocene supported catalyst of claim 1, wherein the compound represented by the Chemical Formula 2c is any one of the following structural formulae:
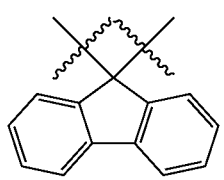 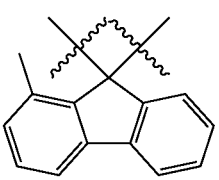
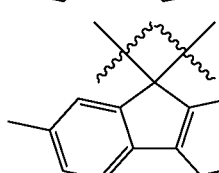 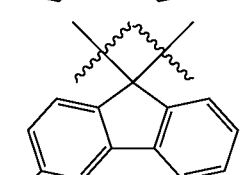
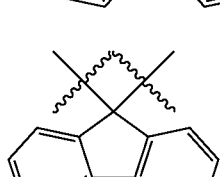 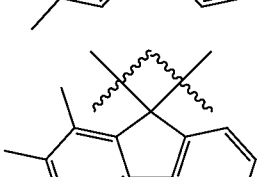
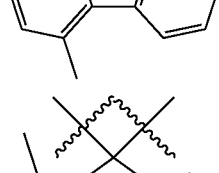 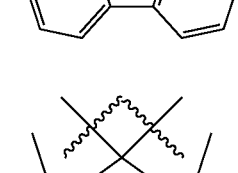
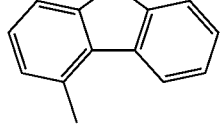 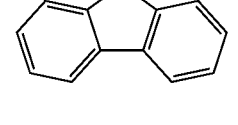
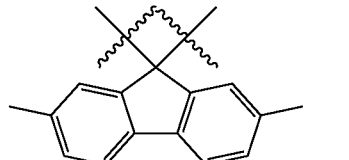
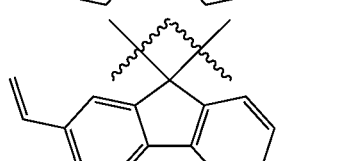
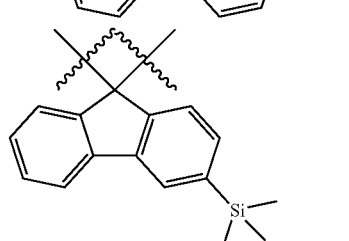
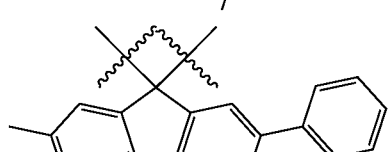
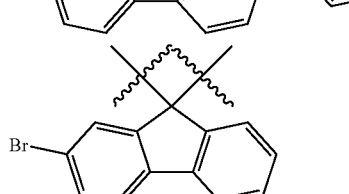
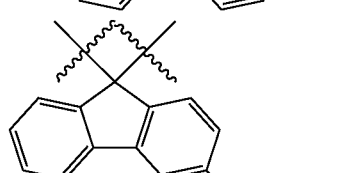
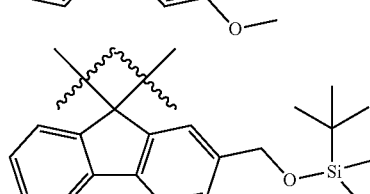
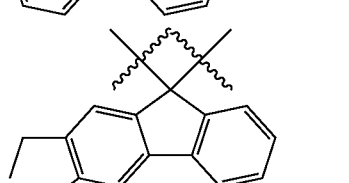
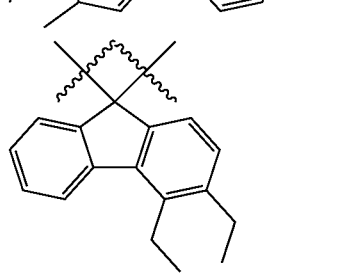

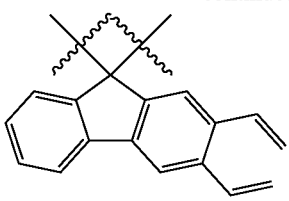

7. The metallocene supported catalyst of claim 1, wherein the cocatalyst compound comprises one or more of compounds represented by the following Chemical Formula 3, Chemical Formula 4, and Chemical Formula 5:

—[Al($R_a$)—O]$_n$—     [Chemical Formula 3]

in Chemical Formula 3,
$R_a$ are the same as or different from each other, and each independently halogen; C1 to C20 hydrocarbon; or halogen-substituted C1 to C20 hydrocarbon; and
n is an integer of 2 or more;

J($R_b$)$_3$     [Chemical Formula 4]

in Chemical Formula 4,
$R_b$ are the same as defined in Chemical Formula 3; and
J is aluminum or boron;

[E-H]+[ZA$_4$]- or [E]+[ZA$_4$]-     [Chemical Formula 5]

in Chemical Formula 5,
E is a neutral or cationic Lewis acid;
H is a hydrogen atom;
Z is a Group 13 element; and
A are the same as or different from each other, and each independently a C6 to C20 aryl group or a C1 to C20 alkyl group, of which one or more hydrogen atoms are substituted or unsubstituted with halogen, C1 to C20 hydrocarbon, alkoxy, or phenoxy.

8. The metallocene supported catalyst of claim 1, wherein the support is one or more selected from the group consisting of silica, silica-alumina, and silica-magnesia.

9. The metallocene supported catalyst of claim 1, wherein a weight ratio of the transition metal of the metallocene compound to the support is 1:10 to 1:1,000.

10. The metallocene supported catalyst of claim 1, wherein a weight ratio of the cocatalyst compound to the support is 1:1 to 1:100.

11. A method for preparing a polyolefin, the method comprising polymerizing olefin-based monomers in the presence of the metallocene supported catalyst of claim 1.

12. The method of claim 11, wherein the polymerization is performed by a solution polymerization process, a slurry process, or a gas phase process.

13. The method of claim 11, wherein the olefin-based monomer comprises one or more monomers selected from the group consisting of ethylene, propylene, 1-butene, 1-hexene, 1-octene, 1-pentene, 4-methyl-1-pentene, 1-heptene, 1-decene, 1-undecene, 1-dodecene, norbornene, ethylidenenorbornene, styrene, alpha-methylstyrene, and 3-chloromethylstyrene.

* * * * *